US011466263B2

(12) United States Patent
Duffy et al.

(10) Patent No.: US 11,466,263 B2
(45) Date of Patent: *Oct. 11, 2022

(54) DIAGNOSTIC APPARATUS TO EXTRACT NUCLEIC ACIDS INCLUDING A MAGNETIC ASSEMBLY AND A HEATER ASSEMBLY

(71) Applicant: HandyLab, Inc., Franklin Lakes, NJ (US)

(72) Inventors: Patrick Duffy, Whitmore Lake, MI (US); Kerry Wilson, Elkhart, IN (US); Kalyan Handique, Ypsilanti, MI (US); Jeff Williams, Chelsea, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/953,118

(22) Filed: Nov. 19, 2020

(65) Prior Publication Data

US 2021/0317437 A1 Oct. 14, 2021

Related U.S. Application Data

(60) Continuation of application No. 16/246,782, filed on Jan. 14, 2019, now Pat. No. 10,844,368, which is a
(Continued)

(51) Int. Cl.
*C12N 15/10* (2006.01)
*B01L 3/00* (2006.01)
(Continued)

(52) U.S. Cl.
CPC ........ *C12N 15/1003* (2013.01); *B01L 3/5082* (2013.01); *B01L 7/52* (2013.01);
(Continued)

(58) Field of Classification Search
CPC ...... B01L 2200/16; B01L 3/5082; B01L 7/52; B01L 9/06; B01L 9/527; C12N 15/1003;
(Continued)

(56) References Cited

U.S. PATENT DOCUMENTS

D189,404 S    12/1960 Nicolle
3,050,239 A    8/1962 Williams
(Continued)

FOREIGN PATENT DOCUMENTS

AU    1357102    3/2002
AU    3557502    7/2002
(Continued)

OTHER PUBLICATIONS

Allemand et al., "pH-Dependent Specific Binding and Combing of DNA", Biophys J. (1997) 73(4):2064-2070.
(Continued)

*Primary Examiner* — Maureen Wallenhorst
(74) *Attorney, Agent, or Firm* — Knobbe, Martens, Olson & Bear, LLP

(57) ABSTRACT

A rack for holding samples and various reagents, wherein the rack may be used for loading the samples and reagents prior to using the reagents. The rack accepts complementary reagent holders, each of which contain a set of reagents for carrying out a predetermined processing operation, such as preparing biological samples for amplifying and detecting polynucleotides extracted from the samples.

20 Claims, 18 Drawing Sheets

Related U.S. Application Data continuation of application No. 15/017,977, filed on Feb. 8, 2016, now Pat. No. 10,179,910, which is a division of application No. 13/474,980, filed on May 18, 2012, now abandoned, which is a continuation of application No. 12/178,584, filed on Jul. 23, 2008, now Pat. No. 8,182,763, which is a continuation-in-part of application No. 12/173,023, filed on Jul. 14, 2008, now Pat. No. 8,133,671, said application No. 12/178,584 is a continuation-in-part of application No. 12/218,498, filed on Jul. 14, 2008, now Pat. No. 9,186,677.

(60) Provisional application No. 60/959,437, filed on Jul. 13, 2007.

(51) Int. Cl.
| | | |
|---|---|---|
| *B01L 7/00* | (2006.01) | |
| *B01L 9/00* | (2006.01) | |
| *B01L 9/06* | (2006.01) | |
| *G01N 35/00* | (2006.01) | |
| *G01N 35/02* | (2006.01) | |
| *G01N 35/10* | (2006.01) | |
| *F16K 99/00* | (2006.01) | |
| *G01N 35/04* | (2006.01) | |

(52) U.S. Cl.
CPC ............... *B01L 9/06* (2013.01); *B01L 9/527* (2013.01); *F16K 99/0001* (2013.01); *F16K 99/003* (2013.01); *F16K 99/0032* (2013.01); *F16K 99/0044* (2013.01); *F16K 99/0061* (2013.01); *G01N 35/0099* (2013.01); *G01N 35/026* (2013.01); *G01N 35/1002* (2013.01); *B01L 2200/16* (2013.01); *F16K 2099/0084* (2013.01); *G01N 2035/00772* (2013.01); *G01N 2035/00801* (2013.01); *G01N 2035/00881* (2013.01); *G01N 2035/0493* (2013.01); *Y10T 436/113332* (2015.01)

(58) Field of Classification Search
CPC .......... G01N 2035/00772; G01N 2035/00801; G01N 2035/00881; G01N 2035/0493; G01N 35/0099; G01N 35/026; G01N 35/1002; Y10T 436/11; Y10T 436/113332; Y10T 436/25; Y10T 436/25375; Y10T 436/255; Y10T 436/2575; B03C 1/01; B03C 1/0332; B03C 1/288; B03C 1/30; B03C 2201/18; B03C 2201/26; F16K 2099/0084
USPC ..... 436/43, 47, 94, 147, 174, 177, 178, 180; 422/63, 65, 68.1, 509, 527, 560, 561, 422/562, 565; 435/287.1, 287.2
See application file for complete search history.

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| 4,698,302 A | 10/1987 | Whitehead et al. |
| D292,735 S | 11/1987 | Lovborg |
| 4,720,374 A | 1/1988 | Ramachandran |
| 4,724,207 A | 2/1988 | Hou et al. |
| 4,795,698 A | 1/1989 | Owen et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,889,818 A | 12/1989 | Gelfand et al. |
| 4,895,650 A | 1/1990 | Wang |
| 4,902,624 A | 2/1990 | Columbus et al. |
| 4,914,710 A | 4/1990 | Ward et al. |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,948,561 A | 8/1990 | Hinckley et al. |
| 4,949,742 A | 8/1990 | Rando et al. |
| D310,413 S | 9/1990 | Bigler et al. |
| 4,963,498 A | 10/1990 | Hillman |
| 4,965,188 A | 10/1990 | Mullis et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 4,994,373 A | 2/1991 | Stavrianopoulos et al. |
| 4,997,772 A | 3/1991 | Sutton et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,089,233 A | 2/1992 | DeVaney, Jr. et al. |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,147,777 A | 9/1992 | Sutton et al. |
| 5,155,166 A | 10/1992 | Danielson et al. |
| 5,169,512 A | 12/1992 | Wiedenmann et al. |
| 5,173,269 A | 12/1992 | Mon et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |

(56) References Cited

U.S. PATENT DOCUMENTS

| | | |
|---|---|---|
| 5,217,694 A | 6/1993 | Gibler et al. |
| 5,223,226 A | 6/1993 | Wittmer et al. |
| 5,229,297 A | 7/1993 | Schnipelsky et al. |
| 5,231,015 A | 7/1993 | Cummins et al. |
| D338,275 S | 8/1993 | Fischer et al. |
| 5,234,809 A | 8/1993 | Boom et al. |
| 5,250,263 A | 10/1993 | Manz |
| 5,252,743 A | 10/1993 | Barrett et al. |
| 5,256,376 A | 10/1993 | Callan et al. |
| 5,273,716 A | 12/1993 | Northrup et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,334,499 A | 8/1994 | Burdick et al. |
| 5,338,671 A | 8/1994 | Scalice et al. |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,384,499 A | 1/1995 | Pedersen et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,466,574 A | 11/1995 | Liberti et al. |
| 5,474,796 A | 12/1995 | Brennan |
| 5,475,487 A | 12/1995 | Mariella, Jr. et al. |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,576,218 A | 11/1996 | Zurek et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,654,141 A | 8/1997 | Mariani et al. |
| 5,658,515 A | 8/1997 | Lee et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,683,659 A | 11/1997 | Hovatter |
| 5,699,157 A | 12/1997 | Parce et al. |
| 5,700,637 A | 12/1997 | Southern |
| 5,705,813 A | 1/1998 | Apffel et al. |
| 5,720,923 A | 2/1998 | Haff et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,819,749 A | 10/1998 | Lee et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |

(56) References Cited

U.S. PATENT DOCUMENTS

| | | |
|---|---|---|
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,911,737 A | 6/1999 | Lee et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,161 A | 7/1999 | Krulevitch et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| 5,944,717 A | 8/1999 | Lee et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,349 A | 9/1999 | Petersen et al. |
| 5,958,694 A | 9/1999 | Nikiforov |
| 5,959,221 A | 9/1999 | Boyd et al. |
| 5,959,291 A | 9/1999 | Jensen |
| 5,935,522 A | 10/1999 | Swerdlow et al. |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,985,651 A | 11/1999 | Hunicke-Smith |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,450 A | 12/1999 | Northrup et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,043,880 A | 3/2000 | Andrews et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,751 A | 5/2000 | Neukermans |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,143,547 A | 11/2000 | Hsu |
| 6,149,787 A | 11/2000 | Chow et al. |
| 6,149,872 A | 11/2000 | Mack et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,203,759 B1 | 3/2001 | Pelc et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |

(56) References Cited

U.S. PATENT DOCUMENTS

| | | |
|---|---|---|
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,300,124 B1 | 10/2001 | Blumenfeld et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,319,474 B1 | 11/2001 | Krulevitch et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,047 B2 | 9/2002 | Dattagupta et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,186 B1 | 1/2003 | Zou et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,181 B1 | 2/2003 | Northrup et al. |
| 6,521,188 B1 | 2/2003 | Webster |
| 6,524,456 B1 | 2/2003 | Ramsey et al. |
| 6,524,532 B1 | 2/2003 | Northrup |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,432 B1 | 3/2003 | Schneider et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,565,815 B1 | 5/2003 | Chang et al. |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,605,475 B1 | 8/2003 | Taylor et al. |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,133 B2 | 12/2003 | Knapp et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,762,049 B2 | 7/2004 | Zou et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |

(56) References Cited

U.S. PATENT DOCUMENTS

| | | |
|---|---|---|
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Björnson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,940,598 B2 | 9/2005 | Christel et al. |
| 6,942,771 B1 | 9/2005 | Kayyem |
| 6,951,632 B2 | 10/2005 | Unger et al. |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,979,424 B2 | 12/2005 | Northrup et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,892 B2 | 10/2006 | Ammann et al. |
| 7,118,910 B2 | 10/2006 | Unger et al. |
| 7,122,799 B2 | 10/2006 | Hsieh et al. |
| 7,135,144 B2 | 11/2006 | Christel et al. |
| 7,138,032 B2 | 11/2006 | Gandhi et al. |
| D534,280 S | 12/2006 | Gomm et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,601 B1 | 1/2007 | Northrup et al. |
| 7,169,618 B2 | 1/2007 | Skold |
| D537,951 S | 3/2007 | Okamoto et al. |
| D538,436 S | 3/2007 | Patadia et al. |
| 7,188,001 B2 | 3/2007 | Young et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,255,833 B2 | 8/2007 | Chang et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| 7,297,313 B1 | 11/2007 | Northrup et al. |
| D556,914 S | 12/2007 | Okamoto et al. |
| 7,303,727 B1 | 12/2007 | Dubrow et al. |
| D559,995 S | 1/2008 | Handique et al. |
| 7,315,376 B2 | 1/2008 | Bickmore et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| 7,578,976 B1 | 8/2009 | Northrup et al. |
| D599,234 S | 9/2009 | Ito |
| 7,595,197 B2 | 9/2009 | Brasseur |
| 7,604,938 B2 | 10/2009 | Takahashi et al. |
| 7,622,296 B2 | 11/2009 | Joseph et al. |
| 7,628,902 B2 | 12/2009 | Knowlton et al. |
| 7,633,606 B2 | 12/2009 | Northrup et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,705,739 B2 | 4/2010 | Northrup et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,785,868 B2 | 8/2010 | Yuan et al. |

(56) References Cited

U.S. PATENT DOCUMENTS

| | | |
|---|---|---|
| D628,305 S | 11/2010 | Gorrec et al. |
| 7,829,025 B2 | 11/2010 | Ganesan et al. |
| 7,858,366 B2 | 12/2010 | Northrup et al. |
| 7,867,776 B2 | 1/2011 | Kennedy et al. |
| 7,892,819 B2 | 2/2011 | Wilding et al. |
| D637,737 S | 5/2011 | Wilson et al. |
| 7,955,864 B2 | 6/2011 | Cox et al. |
| 7,987,022 B2 | 7/2011 | Handique et al. |
| 7,998,708 B2 | 8/2011 | Handique et al. |
| 8,053,214 B2 | 11/2011 | Northrup |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,592,157 B2 | 11/2013 | Petersen et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,765,454 B2 | 7/2014 | Zhou et al. |
| 8,768,517 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,234,236 B2 | 1/2016 | Thomas et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,789,481 B2 | 10/2017 | Petersen et al. |
| 9,802,199 B2 | 10/2017 | Handique et al. |
| 9,815,057 B2 | 11/2017 | Handique |
| 9,958,466 B2 | 5/2018 | Dalbert et al. |
| 10,065,185 B2 | 9/2018 | Handique |
| 10,071,376 B2 | 9/2018 | Williams et al. |
| 10,076,754 B2 | 9/2018 | Lentz et al. |
| 10,100,302 B2 | 10/2018 | Brahmasandra et al. |
| 10,139,012 B2 | 11/2018 | Handique |
| 10,179,910 B2 | 1/2019 | Duffy et al. |
| 10,234,474 B2 | 3/2019 | Williams et al. |
| 10,351,901 B2 | 7/2019 | Ganesan et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,571,935 B2 | 2/2020 | Handique et al. |
| 10,590,410 B2 | 3/2020 | Brahmasandra et al. |
| 10,604,788 B2 | 3/2020 | Wu et al. |
| 10,619,191 B2 | 4/2020 | Ganesan et al. |
| 10,625,261 B2 | 4/2020 | Williams et al. |
| 10,625,262 B2 | 4/2020 | Williams et al. |
| 10,632,466 B1 | 4/2020 | Williams et al. |
| 10,695,764 B2 | 6/2020 | Handique et al. |
| 10,710,069 B2 | 7/2020 | Handique et al. |
| 10,717,085 B2 | 7/2020 | Williams et al. |
| 10,731,201 B2 | 8/2020 | Handique et al. |
| 10,781,482 B2 | 9/2020 | Gubatayao et al. |
| 10,799,862 B2 | 10/2020 | Handique et al. |
| 10,821,436 B2 | 11/2020 | Handique et al. |
| 10,821,446 B1 | 11/2020 | Handique et al. |
| 10,822,644 B2 | 11/2020 | Steel et al. |
| 10,843,188 B2 | 11/2020 | Handique et al. |
| 10,844,368 B2 * | 11/2020 | Duffy .................. B01L 7/52 |
| 10,857,535 B2 | 12/2020 | Handique et al. |
| 10,865,437 B2 | 12/2020 | Handique et al. |
| 10,875,022 B2 * | 12/2020 | Williams ............ F16K 99/0044 |
| 10,900,066 B2 | 1/2021 | Handique et al. |
| 10,913,061 B2 | 2/2021 | Handique et al. |
| 11,060,082 B2 | 7/2021 | Brahmasandra et al. |
| 11,078,523 B2 | 8/2021 | Handique et al. |
| 11,085,069 B2 | 8/2021 | Handique et al. |
| 11,141,734 B2 | 10/2021 | Handique et al. |
| 11,142,785 B2 | 10/2021 | Handique et al. |
| 11,254,927 B2 | 2/2022 | Brahmasandra et al. |
| 11,266,987 B2 | 3/2022 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0018513 A1 | 8/2001 | Baker |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0051340 A1 | 12/2001 | Singh et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0047003 A1 | 4/2002 | Bedingham et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0086443 A1 | 7/2002 | Bamdad |
| 2002/0090320 A1 | 7/2002 | Burow et al. |
| 2002/0092767 A1 | 7/2002 | Bjornson et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0143297 A1 | 10/2002 | Francavilla et al. |
| 2002/0155010 A1 | 10/2002 | Karp et al. |
| 2002/0155477 A1 | 10/2002 | Ito |
| 2002/0169518 A1 | 11/2002 | Luoma et al. |

(56) References Cited

U.S. PATENT DOCUMENTS

| | | |
|---|---|---|
| 2002/0173032 A1 | 11/2002 | Zou et al. |
| 2002/0176804 A1 | 11/2002 | Strand et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0008320 A1 | 1/2003 | Baker |
| 2003/0019522 A1 | 1/2003 | Parunak |
| 2003/0022392 A1 | 1/2003 | Hudak |
| 2003/0036067 A1 | 2/2003 | Schwartz |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0072683 A1 | 4/2003 | Stewart et al. |
| 2003/0073106 A1 | 4/2003 | Johansen et al. |
| 2003/0073110 A1 | 4/2003 | Aritomi et al. |
| 2003/0083686 A1 | 5/2003 | Freeman et al. |
| 2003/0087300 A1 | 5/2003 | Knapp et al. |
| 2003/0088657 A1 | 5/2003 | Eggers |
| 2003/0096310 A1 | 5/2003 | Hansen et al. |
| 2003/0099954 A1 | 5/2003 | Miltenyi et al. |
| 2003/0124611 A1 | 7/2003 | Schwartz |
| 2003/0127327 A1 | 7/2003 | Kurnik |
| 2003/0134333 A1 | 7/2003 | Dehlinger et al. |
| 2003/0136679 A1 | 7/2003 | Bohn et al. |
| 2003/0156991 A1 | 8/2003 | Halas et al. |
| 2003/0180192 A1 | 9/2003 | Seippel |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0043479 A1 | 3/2004 | Briscoe et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0076996 A1 | 4/2004 | Kondo et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0171515 A1 | 9/2004 | Hamers et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0019902 A1 | 1/2005 | Mathies et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0130198 A1 | 6/2005 | Ammann et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0205788 A1 | 9/2005 | Itoh |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0239127 A1 | 10/2005 | Ammann et al. |
| 2005/0266489 A1 | 12/2005 | Ammann et al. |
| 2005/0276728 A1 | 12/2005 | Muller-Cohn et al. |
| 2006/0002817 A1 | 1/2006 | Bohm et al. |
| 2006/0003373 A1 | 1/2006 | Ammann et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0058519 A1 | 3/2006 | Deggerdal et al. |
| 2006/0062696 A1 | 3/2006 | Chow et al. |
| 2006/0081539 A1 | 4/2006 | Safar et al. |
| 2006/0094004 A1 | 5/2006 | Nakajima et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0154341 A1 | 7/2006 | Chen |
| 2006/0165558 A1 | 7/2006 | Witty et al. |
| 2006/0165559 A1 | 7/2006 | Greenstein et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0014695 A1 | 1/2007 | Yue et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077643 A1 | 4/2007 | Nakamura et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178603 A1 | 8/2007 | Takii et al. |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |

(56) References Cited

U.S. PATENT DOCUMENTS

| | | |
|---|---|---|
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0248958 A1 | 10/2007 | Jovanovich et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0056948 A1 | 3/2008 | Dale et al. |
| 2008/0069729 A1 | 3/2008 | McNeely |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0176230 A1 | 7/2008 | Owen et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0257882 A1 | 10/2008 | Turner |
| 2008/0280285 A1 | 11/2008 | Chen et al. |
| 2008/0308500 A1 | 12/2008 | Brassard |
| 2009/0047180 A1 | 2/2009 | Kawahara |
| 2009/0066339 A1 | 3/2009 | Glezer et al. |
| 2009/0136385 A1 | 5/2009 | Handique et al. |
| 2009/0148933 A1 | 6/2009 | Battrell et al. |
| 2009/0189089 A1 | 7/2009 | Bedingham et al. |
| 2009/0223925 A1 | 9/2009 | Morse et al. |
| 2009/0325164 A1 | 12/2009 | Vossenaar et al. |
| 2009/0325276 A1 | 12/2009 | Battrell et al. |
| 2010/0009343 A1 | 1/2010 | Fischer et al. |
| 2010/0009351 A1 | 1/2010 | Brahmasandra et al. |
| 2010/0120129 A1 | 5/2010 | Amshey et al. |
| 2010/0233763 A1 | 9/2010 | Shigeura et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0060136 A1 | 3/2011 | Matsunaga et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0287447 A1 | 11/2011 | Norderhaug |
| 2011/0300033 A1 | 12/2011 | Battisti |
| 2012/0122231 A1 | 5/2012 | Tajima |
| 2012/0160826 A1 | 6/2012 | Handique |
| 2012/0171678 A1 | 7/2012 | Maltezos et al. |
| 2012/0258463 A1 | 10/2012 | Duffy et al. |
| 2013/0183769 A1 | 7/2013 | Tajima |
| 2013/0210127 A1 | 8/2013 | Williams et al. |
| 2013/0315800 A1 | 11/2013 | Yin et al. |
| 2014/0030798 A1 | 1/2014 | Wu et al. |
| 2014/0120544 A1 | 5/2014 | Brahmasandra et al. |
| 2014/0227710 A1 | 8/2014 | Handique et al. |
| 2014/0329301 A1 | 11/2014 | Handique et al. |
| 2015/0045234 A1 | 2/2015 | Stone et al. |
| 2015/0174579 A1 | 6/2015 | Iten et al. |
| 2015/0315631 A1 | 11/2015 | Handique et al. |
| 2016/0038942 A1 | 2/2016 | Roberts |
| 2017/0275702 A1 | 9/2017 | Dahiya et al. |
| 2018/0333722 A1 | 11/2018 | Handique |
| 2019/0054467 A1 | 2/2019 | Handique |
| 2019/0144849 A1 | 5/2019 | Duffy et al. |
| 2019/0145546 A1 | 5/2019 | Handique |
| 2019/0151854 A1 | 5/2019 | Baum et al. |
| 2019/0154719 A1 | 5/2019 | LaChance et al. |
| 2019/0284606 A1 | 9/2019 | Wu et al. |
| 2019/0324050 A1 | 10/2019 | Williams et al. |
| 2020/0139363 A1 | 5/2020 | Handique et al. |
| 2020/0291388 A1 | 9/2020 | Brahmasandra et al. |
| 2021/0001334 A1 | 1/2021 | Handique et al. |
| 2021/0047676 A1 | 2/2021 | Wu et al. |
| 2021/0071234 A1 | 3/2021 | Gubatayao et al. |
| 2021/0121887 A1 | 4/2021 | Handique et al. |
| 2021/0123090 A1 | 4/2021 | Handique et al. |
| 2021/0147923 A1 | 5/2021 | Steel et al. |
| 2021/0276008 A1 | 9/2021 | Handique et al. |
| 2021/0299663 A1 | 9/2021 | Handique |
| 2021/0317437 A1 | 10/2021 | Duffy et al. |
| 2021/0362155 A1 | 11/2021 | Williams et al. |
| 2022/0136034 A1 | 5/2022 | Handique et al. |

FOREIGN PATENT DOCUMENTS

| | | |
|---|---|---|
| AU | 4437602 | 7/2002 |
| AU | 4437702 | 7/2002 |
| AU | 764319 B2 | 8/2003 |
| CA | 2574107 | 9/1998 |
| CA | 2294819 | 1/1999 |
| CN | 1934451 | 3/2007 |
| CN | 1312287 C | 4/2007 |
| CN | 1942590 A | 4/2007 |
| CN | 1968754 A | 5/2007 |
| CN | 101466848 | 6/2009 |
| CN | 101522909 | 9/2009 |
| CN | 103540518 | 1/2014 |
| DE | 19755479 A1 | 6/1999 |
| DE | 19929734 | 12/1999 |
| DE | 19833293 C1 | 1/2000 |
| EP | 0136126 A2 | 4/1985 |
| EP | 0365828 A2 | 5/1990 |
| EP | 0483620 A2 | 5/1992 |
| EP | 0402994 B1 | 11/1994 |
| EP | 0393744 B1 | 1/1995 |
| EP | 0688602 A2 | 12/1995 |
| EP | 0707077 A2 | 4/1996 |
| EP | 0698046 B1 | 3/1997 |
| EP | 0766256 | 4/1997 |
| EP | 0772494 B1 | 5/1997 |
| EP | 0810030 A1 | 12/1997 |
| EP | 1059458 A2 | 12/2000 |
| EP | 1064090 A1 | 1/2001 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1621890 A1 | 2/2006 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H08-337116 | 12/1996 |
| JP | H09-304385 | 11/1997 |
| JP | H09-325151 | 12/1997 |
| JP | 2001-502790 | 1/1998 |
| JP | H01-219669 | 9/1998 |
| JP | H10-327515 | 12/1998 |
| JP | H11-009258 | 1/1999 |
| JP | H11-501504 | 2/1999 |
| JP | H11-503315 | 3/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2000-514928 | 11/2000 |
| JP | 2001-502319 | 2/2001 |

(56) References Cited

FOREIGN PATENT DOCUMENTS

| | | |
|---|---|---|
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-283728 A | 10/2004 |
| JP | 2004-531360 A | 10/2004 |
| JP | 2004-533838 | 11/2004 |
| JP | 2004-534157 | 11/2004 |
| JP | 2004-361421 | 12/2004 |
| JP | 2004-536291 | 12/2004 |
| JP | 2004-536689 A | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-519751 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-055837 A | 3/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-024742 A | 2/2007 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2007-535933 | 12/2007 |
| JP | 2009-515140 | 4/2009 |
| JP | 2009-542207 | 12/2009 |
| JP | 3193848 U | 10/2014 |
| KR | 1020060044489 A | 5/2006 |
| RU | 2418633 C2 | 5/2011 |
| WO | WO 1988/006633 | 9/1988 |
| WO | WO 1990/012350 | 10/1990 |
| WO | WO 1992/005443 | 4/1992 |
| WO | WO 1994/005414 | 3/1994 |
| WO | WO 1994/011103 | 5/1994 |
| WO | WO 1995/033846 | 12/1995 |
| WO | WO 1996/000228 | 1/1996 |
| WO | WO 1996/004547 | 2/1996 |
| WO | WO 1996/018731 | 6/1996 |
| WO | WO 1996/039547 | 12/1996 |
| WO | WO 1997/005492 | 2/1997 |
| WO | WO 1997/016835 | 5/1997 |
| WO | WO 1997/021090 | 6/1997 |
| WO | WO 1997/022825 | 6/1997 |
| WO | WO 1997/027324 | 7/1997 |
| WO | WO 1998/000231 | 1/1998 |
| WO | WO 1998/007019 | 2/1998 |
| WO | WO 1998/022625 | 5/1998 |
| WO | WO 1998/035013 | 8/1998 |
| WO | WO 1998/038487 | 9/1998 |
| WO | WO 1998/049548 | 11/1998 |
| WO | WO 1998/050147 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 1999/060397 | 11/1999 |
| WO | WO 2000/022436 | 4/2000 |
| WO | WO 2000/066783 | 11/2000 |
| WO | WO 2000/073412 | 12/2000 |
| WO | WO 2000/075623 | 12/2000 |
| WO | WO 2000/078455 | 12/2000 |
| WO | WO 2001/005510 | 1/2001 |
| WO | WO 2001/014931 | 3/2001 |
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/046474 | 6/2001 |
| WO | WO 2001/054813 | 8/2001 |
| WO | WO 2001/089681 | 11/2001 |
| WO | WO 2001/089705 | 11/2001 |
| WO | WO 2001/092569 | 12/2001 |
| WO | WO 2002/043864 | 6/2002 |
| WO | WO 2002/048164 | 6/2002 |
| WO | WO 2002/052002 | 7/2002 |
| WO | WO 2002/072264 | 9/2002 |
| WO | WO 2002/078845 | 10/2002 |
| WO | WO 2002/086454 | 10/2002 |
| WO | WO 2002/094185 | 11/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |
| WO | WO 2003/076661 | 9/2003 |
| WO | WO 2003/078065 | 9/2003 |
| WO | WO 2003/080868 | 10/2003 |
| WO | WO 2003/087410 | 10/2003 |
| WO | WO 2004/007081 | 1/2004 |
| WO | WO 2004/010760 | 2/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/094981 | 10/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |

(56) References Cited

FOREIGN PATENT DOCUMENTS

| | | |
|---|---|---|
| WO | WO 2006/113198 | 10/2006 |
| WO | WO 2006/118420 | 11/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 2008/030914 | 3/2008 |
| WO | WO 2008/060604 | 5/2008 |
| WO | WO 2008/134470 | 11/2008 |
| WO | WO 2008/149282 | 12/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Altet et al., [Eds.] "Thermal Transfer and Thermal Coupling in IC's", Thermal Testing of Integrated Circuits; Chapter 2 (2002) Springer Science pp. 23-51.
Anderson et al., "Microfluidic biochemical analysis system" Proc. 1997 IEEE Int. Conf. Solid-State Sens. Actual. (1997) pp. 477-480.
Anderson et al., "Advances in Integrated Genetic Analysis" Micro Total Analysis Systems '98 Conference Proceedings, D. Kluwer Academic Publishers (1998) in 6 pages.
Anderson et al., "A Miniature Integrated Device for Automated Multistep Genetic Assays" Nucleic Acids Research (2000) 28(12), i-vi.
Ateya et al., "The good, the bad, and the tiny: a review of microflow cytometry", Anal Bioanal Chem. (2008) 391(5):1485-1498.
Auroux et al., "Miniaturised nucleic acid analysis", Lab Chip. (2004) 4(6):534-546.
Baechi et al., "High-density microvalve arrays for sample processing in PCR chips", Biomed Microdevices. (2001) 3(3):183-190.
Baker M., "Clever PCR: more genotyping, smaller volumes." Nature Methods (May 2010) 70(5):351-356.
Becker H. "Fabrication of Polymer Microfluidic Devices", in Biochip Technology (2001), Chapter 4, pp. 63-96.
Becker H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.
Becker H., "Microfluidics: A Technology Coming of Age", Med Device Technol. (2008) 19(3):21-24.
Becker et al., "Portable CE system with contactless conductivity detection in an injection molded polymer chip for on-site food analysis", SPIE Proceedings MOEMS-MEMS 2008 Micro and Nanofabrication (2008) vol. 6886 in 8 pages.
Becker H., "Hype, hope and hubris: the quest for the killer application in microfluidics", Lab on a Chip, The Royal Society of Chemistry (2009) 9:2119-2122.
Becker H., "Collective Wisdom", Lab on a Chip, The Royal Society of Chemistry (2010) 10:1351-1354.
Belgrader et al., "Rapid PCR for Identity Testing Using a Battery-Powered Miniature Thermal Cycler", J Forensic Sci. (1998) 43(2):315-319.
Belgrader et al., "A minisonicator to rapidly disrupt bacterial spores for DNA analysis.", Anal Chem. (1999) 71(19):4232-4236.
Belgrader et al., "Real-time PCR Analysis on Nucleic Acids Purified from Plasma Using a Silicon Chip", Micro Total Analysis Systems 2000 (pp. 525-528). Springer, Dordrecht.

Belgrader et al., "A microfluidic cartridge to prepare spores for PCR analysis", Biosens Bioelectron. (2000) 14(10-11):849-852.
Belgrader et al., "A Battery-Powered Notebook Thermal Cycler for Rapid Multiplex Real-Time PCR Analysis", Anal Chem. (2001) 73(2):286-289.
Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.
Belgrader et al., "A Rapid, Flow-through, DNA Extraction Module for Integration into Microfluidic Systems", Micro Total Analysis Systems (2002) pp. 697-699). Springer, Dordrecht.
Belgrader et al., "Development of a Battery-Powered Portable Instrumentation for Rapid PCR Analysis", in Integrated Microfabricated Devices, (2002) Ch. 8, pp. 183-206, CRC Press.
Bell M., "Integrated Microsystems in Clinical Chemistry", in Integrated Microfabricated Devices, (2002) Ch. 16, pp. 415-435, CRC Press.
Berthier et al., "Managing evaporation for more robust microscale assays Part 1. Volume loss in high throughput assays", Lab Chip (2008) 8(6):852-859.
Berthier et al., "Managing evaporation for more robust microscale assays Part 2. Characterization of convection and diffusion for cell biology", Lab Chip (2008) 8(6):860-864.
Berthier et al., "Microdrops," in Microfluidics for Biotechnology (2006), Chapter 2, pp. 51-88.
Biomerieux Press Release: "bioMérieux—2018 Financial Results," dated Feb. 27, 2019, accessed at www.biomerieux.com, pp. 13.
Blanchard et al., "Micro structure mechanical failure characterization using rotating Couette flow in a small gap", J Micromech Microengin. (2005) 15(4):792-801.
Blanchard et al., "Single-disk and double-disk viscous micropumps", Sensors and Actuators A (2005) 122:149-158.
Blanchard et al., "Performance and Development of a Miniature Rotary Shaft Pump", J Fluids Eng. (2005) 127(4):752-760.
Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.
Blanchard et al., "Miniature Single-Disk Viscous Pump (Single-DVP), Performance Characterization", J Fluids Eng. (2006) 128(3):602-610.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Brahmasandra et al., "Microfabricated Devices for Integrated DNA Analysis", in Biochip Technology by Cheng et al., [Eds.] (2001) pp. 229-250.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Bu et al., "Design and theoretical evaluation of a novel microfluidic device to be used for PCR", J Micromech Microengin. (2003) 13(4):S125-S130.
Burns et al., "Microfabricated Structures for Integrated DNA Analysis" Proc. Natl. Acad. Sci. USA (May 1996) 93: 5556-5561.
Burns et al., "An Integrated Nanoliter DNA Analysis Device", Science 282:484-487 (1998).
Cady et al., "Real-time PCR detection of Listeria monocytogenes using an integrated microfluidics platform", Sensors Actual B. (2005) 107:332-341.
Carlen et al., "Paraffin Actuated Surface Micromachined Valve," in IEEE MEMS 2000 Conference, Miyazaki, Japan, (Jan. 2000) pp. 381-385.

(56) References Cited

OTHER PUBLICATIONS

Carles et al., "Polymerase Chain Reaction on Microchips" in Methods in Molecular Biology—Microfluidic Techniques, Reviews & Protocols by Minteer S.D. [Ed.] Humana Press (2006), vol. 321; Chapter 11, pp. 131-140.

Chang-Yen et al., "A novel integrated optical dissolved oxygen sensor for cell culture and micro total analysis systems", IEEE Technical Digest MEMS International Conference Jan. 24, 2002, 4 pages.

Chang-Yen et al., "A PDMS microfluidic spotter for fabrication of lipid microarrays", IEEE 3rd EMBS Special Topic Conference May 12-15, 2005; 2 pages.

Chang-Yen et al., "Design and fabrication of a multianalyte-capable optical biosensor using a multiphysics approach", IEEE 3rd EMBS Special Topic Conference May 12-15, 2005; 2 pages.

Chang-Yen et al., "A Novel PDMS Microfluidic Spotter for Fabrication of Protein Chips and Microarrays", IEEE J of Microelectromech Sys. (2006) 15(5): 1145-1151.

Chang-Yen et al., "Design, fabrication, and packaging of a practical multianalyte-capable optical biosensor," J Microlith Microfab Microsyst. (2006) 5(2):021105 in 8 pages.

Chang-Yen et al., "Spin-assembled nanofilms for gaseous oxygen sensing." Sens Actuators B: Chemical (2007), 120(2):426-433.

Chaudhari et al., "Transient Liquid Crystal Thermometry of Microfabricated PCR Vessel Arrays", J Microelectro Sys., (1998) 7(4):345-355.

Chen P-C., "Accelerating micro-scale PCR (polymerase chain reactor) for modular lab-on-a-chip system", LSU Master's Theses—Digital Commons, (2006) 111 pages.

Chen et al., "Total nucleic acid analysis integrated on microfluidic devices," Lab on a Chip. (2007) 7:1413-1423.

Cheng et al., "Biochip-Based Portable Laboratory", Biochip Tech. (2001):269-289.

Cho et al., "A facility for characterizing the steady-state and dynamic thermal performance of microelectromechanical system thermal switches", Rev Sci Instrum. (2008) 79(3):034901-1 to -8.

Chong et al., "Disposable Polydimethylsiloxane Package for 'Bio-Microfluidic System'", IEEE Proceedings Electronic Components and Technology (2005); 5 pages.

Chou et al., "A miniaturized cyclic PCR device—modeling and experiments", Microelec Eng. (2002) 61-62:921-925.

Christel et al., "Nucleic Acid Concentration and PCR for Diagnostic Applications", in Micro Total Analysis Systems. (1998) D.J. Harrison et al. [Eds.] pp. 277-280.

Christel et al., "Rapid, Automated Nucleic Acid Probe Assays Using Silicon Microstructures for Nucleic Acid Concentration", J Biomech Eng. (1999) 121(1):22-27.

Christensen et al., "Characterization of interconnects used in PDMS microfluidic systems", J Micromech Microeng. (2005) 15:928 in 8 pages.

Chung, Y. et al., "Microfluidic chip for high efficiency DNA extraction", Miniaturisation for Chemistry, Biology & Bioengineering, vol. 4, No. 2 (Apr. 2004), pp. 141-147.

Cooley et al., "Applications of Ink-Jet Printing Technology to BioMEMS and Microfluidic Systems", Proceedings, SPIE Conference on Microfluids and BioMEMS, (Oct. 2001), 12 pages.

Crews et al., "Rapid Prototyping of a Continuous-Flow PCR Microchip", Proceedings of the AiChE Annual Meeting(Nov. 15, 2006) (335a) 3 pages.

Crews et al., Thermal gradient PCR in a continuous-flow microchip. In Microfluidics, BioMEMS, and Medical Microsystems V; Jan. 2007; vol. 6465, p. 646504; 12 pages.

Crews et al., "Continuous-flow thermal gradient PCR", Biomed Microdevices. (2008) 10(2):187-195.

Cui et al., "Electrothermal modeling of silicon PCR chips", In MEMS Design, Fabrication, Characterization, and Packaging, (Apr. 2001) (vol. 4407, pp. 275-280.

Cui et al., "Design and Experiment of Silicon PCR Chips," Proc. SPIE 4755, Design, Test, Integration, and Packaging of MEMS/MOEMS 2002, (Apr. 19, 2002) pp. 71-76.

Danaher Press Release: "Danaher to Acquire Cepheid for $53.00 per share, or approximately $4 Billion," dated Sep. 6, 2016, accessed at www.danaher.com, pp. 3.

Demchenko A.P., "The problem of self-calibration of fluorescence signal in microscale sensor systems", Lab Chip. (2005) 5(11):1210-1223.

Dineva et al., "Sample preparation: a challenge in the development of point-of-care nucleic acid-based assays for resource-limited settings", Analyst. (2007) 132(12):1193-1199.

Dishinger et al., "Multiplexed Detection and Applications for Separations on Parallel Microchips", Electrophoresis. (2008) 29(16):3296-3305.

Dittrich et al., "Single-molecule fluorescence detection in microfluidic channels—the Holy Grail in muTAS?", Anal Bioanal Chem. (2005) 382(8):1771-1782.

Dittrich et al., "Lab-on-a-chip: microfluidics in drug discovery", Nat Rev Drug Discov. (2006) 5(3):210-218.

Dunnington et al., "Approaches to Miniaturized High-Throughput Screening of Chemical Libraries", in Integrated Microfabricated Devices, (2002) Ch. 15, pp. 371-414, CRC Press.

Eddings et al., "A PDMS-based gas permeation pump for on-chip fluid handling in microfluidic devices", J Micromech Microengin. (2006) 16(11):2396-2402.

Edwards, "Silicon (Si)," in "Handbook of Optical Constants of Solids" (Ghosh & Palik eds., 1997) in 24 pages.

Edwards et al., "Micro Scale Purification Systems for Biological Sample Preparation", Biomed Microdevices (2001) 3(3):211-218.

Edwards et al., "A microfabricated thermal field-flow fractionation system", Anal Chem. (2002) 74(6):1211-1216.

Ehrlich et al., "Microfluidic devices for DNA analysis", Trends Biotechnol. (1999) 17(8):315-319.

El-Ali et al., "Simulation and experimental validation of a SU-8 based PCR thermocycler chip with integrated heaters and temperature sensor", Sens Actuators A: Physical (2004) 110(1-3):3-10.

Erickson et al., "Joule heating and heat transfer in poly(dimethylsiloxane) microfluidic systems", Lab Chip (2003) 3(3):141-149.

Erickson et al., "Integrated Microfluidic Devices", Analytica Chim Acta. (2004) 507:11-26.

Erill et al., "Development of a CMOS-compatible PCR chip: comparison of design and system strategies", J Micromech Microengin. (2004) 14(11):1-11.

Fair R.B., Digital microfluidics: is a true lab-on-a-chip possible? Microfluidics Nanofluid. (2007) 3:245-281.

Fan et al., "Integrated Plastic Microfluidic Devices for Bacterial Detection", in Integrated Biochips for DNA Analysis by Liu et al. [Eds], (2007) Chapter 6, pp. 78-89.

Fiorini et al., "Disposable microfluidic devices: fabrication, function, and application", Biotechniques (2005) 38(3):429-446.

Frazier et al., "Integrated micromachined components for biological analysis systems", J Micromech. (2000) 1(1):67-83.

Gale et al., "Micromachined electrical field-flow fractionation (mu-EFFF) system", IEEE Trans Biomed Eng. (1998) 45(12):1459-1469.

Gale et al., "Geometric scaling effects in electrical field flow fractionation. 1. Theoretical analysis", Anal Chem. (2001) 73(10):2345-2352.

Gale et al., "BioMEMS Education at Louisiana Tech University", Biomed Microdevices, (2002) 4:223-230.

Gale et al., "Geometric scaling effects in electrical field flow fractionation. 2. Experimental results", Anal Chem. (2002) 74(5):1024-1030.

Gale et al., "Cyclical electrical field flow fractionation", Electrophoresis. (2005) 26(9):1623-1632.

Gale et al., "Low-Cost MEMS Technologies", Elsevier B.V. (2008), Chapter 1.12; pp. 342-372.

Garst et al., "Fabrication of Multilayered Microfluidic 3D Polymer Packages", IEEE Proceedings Electronic Components & Tech, Conference May-Jun. 2005, pp. 603-610.

Gärtner et al., "Methods and instruments for continuous-flow PCR on a chip", Proc. SPIE 6465, Microfluidics, BioMEMS, and Medical Microsystems V, (2007) 646502; 8 pages.

Giordano et al., "Toward an Integrated Electrophoretic Microdevice for Clinical Diagnostics", in Integrated Microfabricated Biodevices:

(56) References Cited

OTHER PUBLICATIONS

Advanced Technologies for Genomics, Drug Discovery, Bioanalysis, and Clinical Diagnostics (2002) Chapter 1; pp. 1-34.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xerography prototyping of microfluidic channels for DNA melting analysis", J Micromech Microengin. (2007) 17(12):2407-2413.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences—University of Oslo; 94 pages.
Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.
Hale et al., "Optical constants of Water in the 200-nm to 200-µm Wavelength Region", Applied Optics, 12(3): 555-563 (1973).
Handal et al., "DNA mutation detection and analysis using miniaturized microfluidic systems", Expert Rev Mol Diagn. (2006) 6(1):29-38.
Handique et al., "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Hansen et al., "Microfluidics in structural biology: smaller, faster . . . better", Curr Opin Struct Biol. (2003) 13(5):538-544.
Harding et al., "DNA isolation using Methidium-Spermine-Sepharose", Meth Enzymol. (1992) 216:29-39.
Harding et al., "Rapid isolation of DNA from complex biological samples using a novel capture reagent—methidium-spermine-sepharose", Nucl Acids Res. (1989) 17(17): 6947-6958.
Harrison et al., "Capillary Electrophoresis and Sample Injection Systems Integrated on a Planar Glass Chip", Anal. Chem., (1992) 64: 1926-1932.
He et al., Microfabricated Filters for Microfluidic Analytical Systems, Analytical Chemistry, American Chemical Society, 1999, vol. 71, No. 7, pp. 1464-1468.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (µIEF) As a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.
Hong et al., "Integrated nanoliter systems", Nat Biotechnol. (2003) 21(10):1179-1183.
Hong et al., "Molecular biology on a microfluidic chip", J Phys.: Condensed Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al., "Enhancement of thermal uniformity for a microthermal cycler and its application for polymerase chain reaction", Sens Actuators B: Chemical. (2008) 130(2):848-856.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Huang et al., "Temperature Uniformity and DNA Amplification Efficiency in Micromachined Glass PCR Chip", TechConnect Briefs; Tech Proc. Of the 2005 NSTI Nanotechnology Conference and Trade Show. (2005) vol. 1:452-455.
Huebner et al., "Microdroplets: A sea of applications?", Lab Chip. (2008) 8(8):1244-1254.
Ibrahim, et al., Real-Time Microchip PCR for Detecting Single-Base Differences in Viral and Human DNA, Analytical Chemistry, American Chemical Society, 1998, 70(9): 2013-2017.
International Preliminary Report on Patentability and Written Opinion dated Jan. 19, 2010 for Application No. PCT/US2008/008640, filed Jul. 14, 2008.
International Preliminary Report on Patentability dated Jan. 19, 2010 for Application No. PCT/US2008/069897, filed Jul. 11, 2008.
International Search Report and Written Opinion dated Apr. 4, 2008 for PCT/US2007/007513, filed Mar. 26, 2007.
International Search Report and Written Opinion dated Jan. 5, 2009 for PCT/US2007/024022, filed Nov. 14, 2007.
International Search Report and Written Opinion, dated Oct. 3, 2008, issued in International Application No. PCT/US2008/069897, filed Jul. 11, 2008.
International Search Report dated Jun. 17, 2009 for Application No. PCT/US2008/008640, filed Jul. 14, 2008.
Iordanov et al., "PCR Array on Chip—Thermal Characterization", IEEE Sensors (2003) Conference Oct. 22-24, 2003; pp. 1045-1048.
Irawan et al., "Cross-Talk Problem on a Fluorescence Multi-Channel Microfluidic Chip System," Biomed Micro. (2005) 7(3):205-211.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.
Jiang et al., "Directing cell migration with asymmetric micropatterns" Proc. Natl. Acad. Sci. USA (2005) 102, 975-978.
Kaigala et al., "An inexpensive and portable microchip-based platform for integrated RT-PCR and capillary electrophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI—Nanotech (2006) vol. 2, pp. 585-588.
Kantak et al.,"Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chemical and Biochem Analysis Sys. (2003) pp. 1199-1202.

(56) References Cited

OTHER PUBLICATIONS

Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.
Kantak et al., "Improved theory of cyclical electrical field flow fractions", Electrophoresis (2006) 27(14):2833-2843.
Karunasiri et al., "Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Khandurina et al., Microfabricated Porous Membrane Structure for Sample Concentration and Electrophoretic Analysis, Analytical Chemistry American Chemical Society, 1999, 71(9): 1815-1819.
Khandurina et al., "Bioanalysis in microfluidic devices," J Chromatography A, (2002) 943:159-183.
Kim et al., "Reduction of Microfluidic End Effects In Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Electrohydrodynamic Generation and Delivery of Monodisperse Picoliter Droplets Using a Poly(dimethylsiloxane) Microchip", Anal Chem. (2006) 78: 8011-8019.
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kopp et al., Chemical Amplification: Continuous-Flow PCR on a Chip, www.sciencemag.org, 1998, vol. 280, pp. 1046-1048.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.
Krishnan et al., "Polymerase chain reaction in high surface-to-volume ratio SiO2 microstructures", Anal Chem. (2004) 76(22):6588-6593.
Kuo et al., "Remnant cationic dendrimers block RNA migration in electrophoresis after monophasic lysis", J Biotech. (2007) 129: 383-390.
Kuswandi et al., "Optical sensing systems for microfluidic devices: a review", Anal Chim Acta. (2007) 601(2):141-155.
Kutter et al., Solid Phase Extraction on Microfluidic Devices, J. Microcolumn Separations, John Wiley & Sons, Inc., 2000, 12(2): 93-97.
Labchem; Sodium Hydroxide, 0,5N (0.5M); Safety Data Sheet, 2015; 8 pages.
Lagally et al., "Monolithic integrated microfluidic DNA amplification and capillary electrophoresis analysis system" Sensors and Actuators B (2000) 63:138-146.
Lagally et al., Single-Molecule DNA Amplification and Analysis in an Integrated Microfluidic Device, Analytical Chemistry, American Chemical Society, 2001, 73(3): 565-570.
Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5'to 3'Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in Human Immunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No. 00EX451; (Oct. 2000) Poster 66, pp. 531-536.
Li PCH., "Micromachining Methods et al." in Microfluidic Lab-on-a-Chip for Chemical and Biological Analysis and Discovery, CRC Press (2005), Chapter 2-3 to 2-5; pp. 10-49.
Li PCH., "Microfluidic Flow" in Microfluidic Lab-on-a-Chip for Chemical and Biological Analysis and Discovery, CRC Press (2005), Chapter 3, pp. 55-99.
Li PCH., "Detection Methods" in Microfluidic Lab-on-a-Chip for Chemical and Biological Analysis and Discovery, CRC Press (2005), Chapter 7, pp. 187-249.
Li PCH., "Applications to Nucleic Acids Analysis" in Microfluidic Lab-on-a-Chip for Chemical and Biological Analysis and Discovery, CRC Press (2005), Chapter 9; pp. 293-325.
Li et al., "A Continuous-Flow Polymerase Chain Reaction Microchip With Regional Velocity Control", J Microelectromech Syst. (2006) 15(1):223-236.
Liao et al., "Miniature RT-PCR system for diagnosis of RNA-based viruses," Nucl Acids Res. (2005) 33(18):e156 in 7 pages.
Lien et al., "Integrated reverse transcription polymerase chain reaction systems for virus detection", Biosens Bioelectron. (2007) 22(8):1739-1748.
Lien et al., "Microfluidic Systems Integrated with a Sample Pretreatment Device for Fast Nucleic-Acid Amplification", J Microelectro Sys. (2008) 17(2):288-301.
Lifesciences et al., "Microfluidics in commercial applications; an industry perspective." Lab Chip (2006) 6:1118-1121.
Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Lin et al., "Simulation and experimental validation of micro polymerase chain reaction chips", Sens Actuators B: Chemical. (2000) 71(1-2):127-133.
Linder et al., "Microfluidics at the Crossroad with Point-of-care Diagnostics", Analyst (2007) 132:1186-1192.
Liu et al., "Integrated portable polymerase chain reaction-capillary electrophoresis microsystem for rapid forensic short tandem repeat typing", Anal Chem. (2007) 79(5):1881-1889.

(56) References Cited

OTHER PUBLICATIONS

Liu et al. [Eds], Integrated Biochips for DNA Analysis—Biotechnology Intelligence Unit; Springer/Landes Bioscience (2007) ISBN:978-0-387-76758-1; 216 pages.
Livache et al., "Polypyrrole DNA chip on a Silicon Device: Example of Hepatitis C Virus Genotyping", Analytical Biochemistry, (1998) 255: 188-194.
Locascio et al., "ANYL 67 Award Address—Microfluidics as a tool to enable research and discovery in the life sciences", Abstract; The 236th ACS National Meeting (Aug. 2008); 2 pages.
Mahjoob et al., "Rapid microfluidic thermal cycler for polymerase chain reaction nucleic acid amplification", Inter'l J Heat Mass Transfer. (2008) 51(9-10):2109-2122.
Malitson, "Interspecimen Comparison of the Refractive Index of Fused Silica," J Optical Society of America, 55:1205-1209 (1965).
Manz et al., "Miniaturized Total Chemical Analysis Systems: a Novel Concept for Chemical Sensing," Sensors and Actuators B1, (1990) 244-248.
Manz et al., "Design of an open-tubular column liquid chromatograph using silicon chip technology" Sensors and Actuators B (1990) 1:249-255.
Manz et al., "Planar chips technology for miniaturization and integration of separation techniques into monitoring systems: Capillary electrophoresis on a chip" Journal of Chromatography A (1992) 593:253-258.
Marcus et al., "Parallel picoliter rt-PCR assays using microfluidics", Anal Chem. (2006) 78(3):956-958.
Mariella R.P. Jr., "Microtechnology", Thrust Area Report FY 96 UCRL-ID-125472; Lawrence Livermore National Lab., CA (Feb. 1997) Chapter 3 in 44 pages.
Mariella R., "Sample preparation: the weak link in microfluidics-based biodetection", Biomed Microdevices. (2008) 10(6):777-784.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
McMillan et al., "Application of advanced microfluidics and rapid PCR to analysis of microbial targets", In Proceedings of the 8th international symposium on microbial ecology (1999), in 13 pages.
Melin et al., "Microfluidic large-scale integration: the evolution of design rules for biological automation", Annu Rev Biophys Biomol Struct. (2007) 36:213-231.
Merugu et al., "High Throughput Separations Using a Microfabricated Serial Electric Split System" (2003), Proceedings of µTAS 2003, 7th International Conference on Miniaturized Chemical and Biochemical Analysis Systems, Oct. 5-9, 2003, Squaw Valley, California; 1191-1194, in 3 pages.
Meyers, R.A., Molecular Biology and Biotechnology: A Comprehensive Desk Reference; VCH Publishers, Inc. New York, NY; (1995) pp. 418-419.
Miao et al., "Low cost micro-PCR array and micro-fluidic integration on single silicon chip", Int'l J Comput Eng Science (2003) 4(2):231-234.
Miao et al., "Flip-Chip packaged micro-plate for low cost thermal multiplexing", Int'l J Comput Eng Science. (2003) 4(2):235-238.
Micheletti et al., "Microscale Bioprocess Optimisation", Curr Opin Biotech. (2006) 17:611-618.
MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.
MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.
MicroTAS 2007., "Micro Total Analysis Systems", Advance Program for the Proceedings 11th Int. Conference on Miniaturized Systems for Chemistry and Life Sciences; Presentations/Posters/Articles for Conference; Paris, France in Oct. 7-11, 2007 in 42 pages.

Minco, "Conductive Heating Technologies for Medical Diagnostic Equipment," (2006) in 13 pages.
Mitchell et al., "Modeling and validation of a molded polycarbonate continuous-flow polymerase chain reaction device," Microfluidics, BioMEMS, and Medical Microsystems, Proc. SPIE (2003) 4982:83-98.
Myers et al., "Innovations in optical microfluidic technologies for point-of-care diagnostics", Lab Chip (2008) 8:2015-2031.
Nakagawa et al., Fabrication of amino silane-coated microchip for DNA extraction from whole blood, J of Biotechnology, Mar. 2, 2005, 116: 105-111.
Namasivayam et al., "Advances in on-chip photodetection for applications in miniaturized genetic analysis systems", J Micromech Microeng. (2004) 14:81-90.
Narayanan et al., "A microfabricated electrical SPLITT system," Lab Chip, (2006) 6:105-114.
Neuzil et al., "Disposable real-time microPCR device: lab-on-a-chip at a low cost," Mol. Biosyst., (2006) 2:292-298.
Neuzil et al., "Ultra fast miniaturized real-time PCR: 40 cycles in less than six minutes," Nucleic Acids Research, (2006) 34(11)e77, in 9 pages.
Nguyen et al. [Eds], "Microfluidics for Internal Flow Control: Microfluidics" in Fundamentals and Applications of Microfluidics; 2nd Edition (2006) Introduction Chapter 1, pp. 1-9.
Nguyen et al. [Eds], "Microfluidics for Internal Flow Control: Microvalves" in Fundamentals and Applications of Microfluidics; (2006) 2nd Edition, Chapter 6, pp. 211-254.
Nguyen et al. [Eds], "Microfluidics for Internal Flow Control: Micropumps" in Fundamentals and Applications of Microfluidics; (2006) 2nd Edition, Chapter 7, pp. 255-309.
Nguyen et al. [Eds], "Microfluidics for Life Sciences and Chemistry: Microdispensers" in Fundamentals and Applications of Microfluidics; (2006), Chapter 11, pp. 395-418.
Nguyen et al. [Eds], "Microfluidics for Life Sciences and Chemistry: Microreactors" in Fundamentals and Applications of Microfluidics; (2006) 2nd Edition, Chapter 13, pp. 443-477.
Ning et al., "Microfabrication Processes for Silicon and Glass Chips", in Biochip Technology, CRC-Press (2006) Chapter 2, pp. 17-38.
Northrup et al., "A MEMS-based Miniature DNA Analysis System," Lawrence Livermore National Laboratory, (1995), submitted to Transducers '95, Stockholm, Sweden, Jun. 25-29, 1995, in 7 pages (Prepublication).
Northrup et al., "Advantages Afforded by Miniaturization and Integration of DNA Analysis Instrumentation," Microreaction Technology, (1998) 278-288.
Northrup et al., A Miniature Analytical Instrument for Nucleic Acids Based on Micromachined Silicon Reaction Chambers, Analytical Chemistry, American Chemical Society, 1998, 70(5): 918-922.
Northrup et al., "A New Generation of PCR Instruments and Nucleic Acid Concentration Systems," in PCR Applications: Protocols for Functional Genomics, (1999), Chapters, pp. 105-125.
Northrup, "Microfluidics, A few good tricks," Nature materials (2004), 3:282-283.
Northrup et al.,"Microfluidics-based integrated airborne pathogen detection systems," Abstract, Proceedings of the SPIE, (2006), vol. 6398, Abstract in 2 pages.
Oh et al., "World-to-chip microfluidic interface with built-in valves for multichamber chip-based PCR assays," Lab Chip, (2005), 5:845-850.
Oh K.W. et al., "A Review of Microvalves", J Micromech Microeng. (2006) 16:R13-R39.
Ohno et al., "Microfluidics: Applications for analytical purposes in chemistry and biochemistry," Electrophoresis (2008), 29:4443-4453.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Pal et al., "Phase Change Microvalve for Integrated Devices", Anal Chem. (2004) 76: 3740-3748.
Pal et al., "An integrated microfluidic for influenza and other genetic analyses," Lab Chip, (2005), 5:1024-1032.

(56) References Cited

OTHER PUBLICATIONS

Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Pamme, "Continuous flow separations in microfluidic devices," Lab Chip, (2007), 7:1644-1659.
Pang et al., "A novel single-chip fabrication technique for three-dimensional MEMS structures," Institute of Microelectronics, Tsinghua University, Beijing, P.R. China, (1998), IEEE, 936-938.
Pang et al., "The Study of Single-Chip Integrated Microfluidic System," Tsinghua University, Beijing, P.R. China, (1998), IEEE, 895-898.
Papautsky et al., "Effects of rectangular microchannel aspect ratio on laminar friction constant", in Microfluidic Devices and Systems II (1999) 3877:147-158.
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Picard et al., Laboratory Detection of Group B *Streptococcus* for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11): 2556-2563.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcription-PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Rhee et al., "Drop Mixing in a Microchannel for Lab-on-a-Chip Applications" Langmuir (2008) 24 (2):590-601.
Roche et al. "Ectodermal commitment of insulin-producing cells derived from mouse embryonic stem cells" Faseb J (2005) 19: 1341-1343.
Rodriguez et al., "Practical integration of polymerase chain reaction amplification and electrophoretic analysis in microfluidic devices for genetic analysis," Electrophoresis, (2003), 24:172-178.
Rohsenow et al. [Eds.], Handbook of Heat Transfer, 3rd Edition McGraw-Hill Publishers (1998) Chapters 1 & 3; pp. 108.
Roper et al., "Advances in Polymer Chain Reaction on Microfluidic Chips," Anal. Chem., (2005), 77:3887-3894.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Ross et al., "Scanning Temperature Gradient Focusing for Simultaneous Concentration and Separation of Complex Samples," Micro Total Analysis Systems 2005, vol. 2, (2005), Proceedings of µTAS 2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Sadler et al., "Thermal Management of BioMEMS: Temperature Control for Ceramic-Based PCR and DNA Detection Devices," IEEE Transactions on Components and Packaging Technologies, (2003) 26(2):309-316.
Sammarco et al., "Thermocapillary Pumping of Discrete Drops in Microfabricated Analysis Devices" AlChE Journal (1999) 45(2): 350-366.
Sanchez et al., "Linear-After-The-Exponential (LATE)-PCR: An advanced method of asymmetric PCR and its uses in quantitative real-time analysis", PNAS (2004) 101(7): 1933-1938.
Sant et al., "An Integrated Optical Detector for Microfabricated Electrical Field Flow Fractionation System," Proceedings of µTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anal Chem. (2006) 78:7978-7985.
Sant et al., "Microscale Field-Flow Fractionation: Theory and Practice", in Microfluidic Technologies for Miniaturized Analysis Systems. (2007) Chapter 12, pp. 4710521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Shen et al., "A microchip-based PCR device using flexible printed circuit technology," Sensors and Actuators B (2005), 105:251-258.
Shoffner et al., Chip PCR.I. Surface Passivation of Microfabricated Silicon-Glass Chips for PCR, Nucleic Acids Research, Oxford University Press, (1996) 24(2): 375-379.
Sia et al., "Microfluidic devices fabricated in poly(dimethylsiloxane) for biological studies," Electrophoresis, (2003), 24:3563-3576.
Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Smith et al., "(576d) Micropatterned fluid lipid bilayers created using a continuous flow microspotter for multi-analyte assays," (2007), Biosensors II, 2007 AlChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), Chapter 10, pp. 97-129.
Squires et al., "Microfluidics: Fluid physics at the nanoliter scale", Rev Modern Phys. (2005) 77(3):977-1026.

(56) References Cited

OTHER PUBLICATIONS

Sundberg et al., "Solution-phase DNA mutation scanning and SNP genotyping by nanoliter melting analysis," Biomed Microdevices, (2007), 9:159-166, in 8 pages.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., "Optimization of the performance of the polymerase chain reaction in silicon-based microstructures" Nucleic Acids Res. (1997) vol. 25, pp. 3164-3168.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Terry et al., "A Gas Chromatographic Air Analyzer Fabricated on a Silicon Wafer" IEEE T Electron Dev (1979) 26:1880-1886.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
Velten et al., "Packaging of Bio-MEMS: Strategies, Technologies, and Applications," IEEE Transactions on Advanced Packaging, (2005) 28(4):533-546.
Vinet et al., "Microarrays and microfluidic devices: miniaturized systems for biological analysis," Microelectronic Engineering, (2002), 61-62:41-47.
Wang, "Survey and Summary, from DNA Biosensors to Gene Chips", Nucleic Acids Research, 28(16):3011-3016, (2000).
Wang et al., "From biochips to laboratory-on-a-chip system", in Genomic Signal Processing and Statistics by Dougherty et al. [Eds]; (2005) Chapters, pp. 163-200.
Wang et al., "A disposable microfluidic cassette for DNA amplification and detection", Lab on a Chip (2006) 6(1):46-53.
Wang et al., "Micromachined Flow-through Polymerase Chain Reaction Chip Utilizing Multiple Membrane-activated Micropumps," (2006), MEMS 2006, Jan. 22-26, 2006, Istanbul, Turkey; 374-377.
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Whitesides G.M., "The origins and the future of microfluidics" Nature (2006) 442(7101):368-373.
Woias P., "Micropumps—past, progress and future prospects" Sensors and Actuators B (2005) 105, 28-38.
Woolley et al., "Functional integration of PCR amplification and capillary electrophoresis in a microfabricated DNA analysis device" Anal. Chem. (1996) vol. 68, pp. 4081-4086.
Woolley A.T., "Integrating Sample Processing and Detection with Microchip Capillary Electrophoresis of DNA", in Integrated Biochips for DNA Analysis by Liu et al. [Eds]; (2007) Chapter 5, pp. 68-77.
Wu et al., "Fabrication of Complex Three-dimensional Microchannel Systems in PDMS" J. Am. Chem. Soc. (2003) 125, 554-559.
Wu et al., "Polycationic dendrimers interact with RNA molecules: polyamine dendrimers inhibit the catalytic activity of Candida ribozymes", Chem Commun. (2005) 3: 313-315.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.
Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., Microfluidic Chips for Viral RNA Extraction & Detection, (2005), 2005 IEEE, 49-52.
Yobas et al., "Nucleic Acid Extraction, Amplification, and Detection on Si-Based Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhang et al., "Temperature analysis of continuous-flow micro-PCR based on FEA," Sensors and Actuators B, (2002), 82:75-81.
Zhang et al., "PCR Microfluidic Devices for DNA Amplification," Biotechnology Advances, 24:243-284 (2006).
Zhang et al., "Continuous-flow PCR Microfluidics for Rapid DNA Amplification Using Thin Film Heater with Low Thermal Mass," Analytical Letters, (2007), 40:1672-1685, in 15 pages.
Zhang et al., "Direct Adsorption and Detection of Proteins, Including Ferritin, onto Microlens Array Patterned Bioarrays," J Am Chem Soc., (2007), 129:9252-9253.
Zhang et al., "Micropumps, microvalves, and micromixers within PCR microfluidic chips: Advances and trends," Biotechnology Advances, (2007), 25:483-514.
Zhang et al., "Miniaturized PCR chips for nucleic acid amplification and analysis: latest advances and future trends," Nucl Acids Res., (2007) 35(13):4223-4237.
Zhang et al., "Parallel DNA amplification by convective polymerase chain reaction with various annealing temperatures on a thermal gradient device," Analytical Biochemistry, (2009) 387:102-112.
Zhao et al., "Heat properties of an integrated micro PCR vessel," Proceedings of SPIE, (2001), International Conference on Sensor Technology, 4414:31-34.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).

(56) References Cited

OTHER PUBLICATIONS

Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR2019-00490) dated Dec. 20, 2018 (85 pages).
Declaration of Michael G. Mauk, Ph.D. in Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Record of Oral Hearing in IPR2019 00488 and IPR2019 00490 held Apr. 21, 2020 (80 pages); Petitioner's Demonstratives for Oral Hearing in IPR2019 00488 and IPR2019 00490 held Apr. 21, 2020 (72 pages); Patent Owner's Demonstratives for Oral Hearing in IPR2019 00488 and IPR2019 00490 held Apr. 21, 2020 (88 pages); Patent Owner's Objections to Petitioner's Oral Hearing Demonstratives in IPR2019 00488 and IPR2019 00490 dated Apr. 16, 2020 (4 pages).
Judgment/Final Written Decision Determining No Challenged Claims Unpatentable in Inter Partes Review of U.S. Pat. No. 7,998,708 (Paper No. 52 in IPR2019-00488) dated Jul. 14, 2020 (43 pages).
Judgment/Final Written Decision Determining No Challenged Claims Unpatentable in Inter Partes Review of U.S. Pat. No. 8,323,900 (Paper No. 51 in IPR2019-00490) dated Jul. 14, 2020 (43 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).
Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
Complaint filed by *Becton, Dickinson et al.,* v. *NeuModx Molecular, Inc.* on Jun. 18, 2019 in U.S. District Court, Delaware, Case #1:19-cv-01126-LPS, Infringement Action involving U.S. Pat. No. 7,998,708; U.S. Pat. No. 8,273,308; U.S. Pat. No. 8,323,900; U.S. Pat. No. 8,415,103; U.S. Pat. No. 8,703,069; and U.S. Pat. No. 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
First Amended and Supplemental Complaint filed by Becton, Dickinson and Company et al. on Jun. 25, 2020 in U.S. District Court, Delaware, Case #1:19-cv-01126-LPS, Infringement Action involving U.S. Pat. No. 7,998,708; U.S. Pat. No. 8,273,308; U.S. Pat. No. 8,323,900; U.S. Pat. No. 8,415,103; U.S. Pat. No. 8,703,069; U.S. Pat. No. 8,709,787; U.S. Pat. No. 10,494,663; U.S. Pat. No. 10,364,456; U.S. Pat. No. 10,443,088; U.S. Pat. No. 10,604,788; U.S. Pat. No. 10,625,261; U.S. Pat. No. 10,625,262; and U.S. Pat. No. 10,632,466 (55 pages).
Answer to First Amended and Supplemental Complaint filed by NeuModx Molecular, Inc. on Jul. 16, 2020 in U.S. District Court, Delaware, Case #1:19-cv-01126-LPS (42 pages).
BDProbeTec™ ET Neisseria gonorrhoeae Amplified DNA Assay Package Insert, Jul. 2010 (13 pages).
BDProbeTec™ ET System Brochure, Aug. 2010 (9 pages).
Benters et al., "Dendrimer-Activated Solid Supports for Nucleic Acid and Protein Microarrays", ChemBioChem (2001) 2(9): 686-694.
Devarakonda et al., "The effect of PAMAM dendrimer generation size and surface functional group on the aqueous solubility of nifedipine", Int J Pharma. 284(1-2): 133-140.
Gill et al., "Nucleic Acid Isothermal Amplification Technologies—A Review", Nucleosides Nucleotides Nucleic Acids, (2008) 27(3): 224-243.
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Rush et al., "Dispersion by Pressure-Driven Flow in Serpentine Microfluidic Channels", Ind Eng Chem Res., (2002) 41: 4652-4662.

(56) References Cited

OTHER PUBLICATIONS

U.S. Appl. No. 60/491,264, filed Jul. 31, 2003 (41 pages).
U.S. Appl. No. 60/491,269, filed Jul. 31, 2003 (52 pages).
U.S. Appl. No. 60/491,539, filed Aug. 1, 2003 (45 pages).
U.S. Appl. No. 60/553,553, filed Mar. 17, 2004 (49 pages).
U.S. Appl. No. 60/726,066, filed Oct. 11, 2005 (54 pages).
U.S. Appl. No. 60/786,007, filed Mar. 24, 2006 (223 pages).
U.S. Appl. No. 60/859,284, filed Nov. 14, 2006 (114 pages).
Walker et al., "Strand displacement amplification—an isothermal, in vitro DNA amplification technique", Nucleic Acids Res. (1992) 20(7): 1691-1696.
Patent Owner's Preliminary Response to Petition for Inter Partes Review of U.S. Pat. No. 8,703,069 (Paper 13 in IPR2020-01095) dated Sep. 17, 2020 (77 pages).
Patent Owner's Preliminary Response to Petition for Inter Partes Review of U.S. Pat. No. 8,273,308 (Paper 13 in IPR2020-01091) dated Sep. 17, 2020 (70 pages).
Patent Owner's Preliminary Response to Petition for Inter Partes Review of U.S. Pat. No. 8,703,069 (Paper 14 in IPR2020-01100) dated Sep. 17, 2020 (59 pages).
Declaration of M. Allen Northrup, Ph.D. in Support of Patent Owner Preliminary Responses in IPR2020-01091, IPR2020-01095 and IPR2020-01100 (Exhibit H2003) dated Sep. 16, 2020 (137 pages).
Patent Owner's Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021-00251) dated Nov. 25, 2020 (117 pages).
Petition for Inter Partes Review of U.S. Pat. No. 10,632,466 (Paper 2 in IPR202-00253) dated Nov. 25, 2020 (121 pages).
Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
Decision Denying Institution of Inter Partes Review of U.S. Pat. No. 8,273,308 (Paper 14 in IPR2020-01083) dated Jan. 7, 2021 (24 pages).
Patent Owner's Preliminary Response to Petition for Inter Partes Review of U.S. Pat. No. 8,415,103 (Paper 20 in IPR2020-01133) dated Jan. 20, 2021 (67 pages).
Patent Owner's Preliminary Response to Petition for Inter Partes Review of U.S. Pat. No. 8,709,787 (Paper 19 in IPR2020-01132) dated Jan. 20, 2021 (78 pages).
Declaration of M. Allen Northrup, Ph.D. in support of Patent Owner Preliminary Responses in IPR2020-01132 and IPR2020-01133 (Exhibit H2016) dated Jan. 20, 2021 (154 pages).
Patent Owner's Preliminary Response to Petition for Inter Partes Review of U.S. Pat. No. 8,415,103 (Paper 19 in IPR2020-01136) dated Jan. 20, 2021 (77 pages).
Patent Owner's Preliminary Response to Petition for Inter Partes Review of U.S. Pat. No. 8,709,787 (Paper 19 in IPR2020-01137) dated Jan. 20, 2021 (69 pages).
Declaration of M. Allen Northrup, Ph.D. in support of Patent Owner Preliminary Responses in IPR2020-01136 and IPR2020-01137 (Exhibit H2016) dated Jan. 20, 2021 (111 pages).
Opening Brief [Corrected] of Appellants Qiagen North American Holdings, Inc. and NeuMoDx Molecular Inc. in Appeals from the USPTO, PTAB, in Nos. IPR2019-00488, IPR2019-00490, IPR2019-01493 and IPR2019-01494 filed Jan. 22, 2021 in U.S. Court of Appeals for the Federal Circuit Case Nos. 20-2249, 20-2250, 20-2273 and 20-2276 (82 pages).
Decision Granting Institution of Inter Partes Review of U.S. Pat. No. 8,709,787 (Paper 20 in IPR2020-01132) dated Apr. 19, 2021 (33 pages).
Decision Denying Institution of Inter Partes Review of U.S. Pat. No. 8,415,103 (Paper 21 in IPR2020-01133) dated Apr. 19, 2021 (24 pages).
Decision Denying Institution of Inter Partes Review of U.S. Pat. No. 8,415,103 (Paper 20 in IPR2020-01136) dated Apr. 19, 2021 (19 pages).
Decision Denying Institution of Inter Partes Review of U.S. Pat. No. 8,709,787 (Paper 20 in IPR2020-01137) dated Apr. 19, 2021 (14 pages).
Patent Owner's Preliminary Response to Petition for Inter Partes Review of U.S. Pat. No. 10,625,262 (Paper 6 in IPR2021-00250) dated Apr. 19, 2021 (71 pages).
Patent Owner's Preliminary Response to Petition for Inter Partes Review of U.S. Pat. No. 10,625,261 (Paper 6 in IPR2021-00251) dated Apr. 19, 2021 (82 pages).
Patent Owner's Preliminary Response to Petition for Inter Partes Review of U.S. Pat. No. 10,632,466 (Paper 6 in IPR2021-00253) dated Apr. 19, 2021 (66 pages).
Declaration of James P. Landers, Ph.D. in support of Patent Owner Preliminary Responses in IPR2021-00250, IPR2021-00251, and IPR2021-00253 (Exhibit H2003) dated Apr. 19, 2021 (189 pages).
Brief for Appellee HandyLab, Inc. in Appeals from the USPTO, PTAB, in Nos. IPR2019-00488, IPR2019-00490, IPR2019-01493 and IPR2019-01494 filed May 24, 2021 in U.S. Court of Appeals for the Federal Circuit Case Nos. 20-2249, 20-2250, 20-2273 and 20-2276 (74 pages).
Reply Brief of Appellants Qiagen North American Holdings, Inc. and NeuMoDx Molecular, Inc. in Appeals from the USPTO, PTAB, in Nos. IPR2019-00488, IPR2019-00490, IPR2019-01493 and IPR2019-01494 filed Jun. 21, 2021 in U.S. Court of Appeals for the Federal Circuit Case Nos. 20-2249, 20-2250, 20-2273 and 20-2276 (44 pages).
Decision Denying Institution of Inter Partes Review of U.S. Pat. No. 10,625,262 (Paper 7 in IPR2021-00250) dated Jul. 15, 2021 (15 pages).
Decision Denying Institution of Inter Partes Review of U.S. Pat. No. 10,632,466 (Paper 7 in IPR2021-00253) dated Jul. 15, 2021 (22 pages).
Decision Denying Institution of Inter Partes Review of U.S. Pat. No. 10,625,261 (Paper 7 in IPR2021-00251) dated Jul. 15, 2021 (24 pages).
Patent Owner's Response in Inter Partes Review of U.S. Pat. No. 8,709,787 and Exhibit List (Paper 29 in IPR 2020-01132) dated Jul. 15, 2021 (87 pages).
Decision Granting Institution of Inter Partes Review of U.S. Pat. No. 8,415,103 on Rehearing (Paper 23 in IPR2020-01133) dated Aug. 6, 2021 (20 pages).
Decision of U.S. Court of Appeal for the Federal Circuit Affirming Inter Partes Review Final Written Decisions Determining No Challenged Claims of U.S. Pat. No. 7,998,708 and U.S. Pat. No. 8,323,900 are Unpatentable (IPR2019-00488, IPR2019-00490, IPR2019-01493, and IPR2019-01494) dated Oct. 29, 2021 (12 pages).
Joint Motion to Terminate Inter Partes Review of U.S. Pat. No. 8,709,787 (Paper 37 in IPR 2020-01132) dated Nov. 15, 2021 (8 pages).
Joint Motion to Terminate Inter Partes Review of U.S. Pat. No. 8,415,103 (Paper 35 in IPR 2020-01133) dated Nov. 15, 2021 (8 pages).

(56) References Cited

OTHER PUBLICATIONS

Defendant NeuModx's Initial Invalidity Contentions filed Sep. 30, 2020 in U.S. District Court, Delaware, Case #1:19-cv-01126-LPS (47 pages).
Defendant NeuModx's Joint Claim Construction Chart [Exhibit N1023] filed Oct. 21, 2020 in U.S. District Court, Delaware, Case #1:19-cv-01126-LPS (25 pages).
Defendant NeuModx's Amended Answer, Affirmative Defenses, and Counterclaims to Plaintiffs' First Amended and Supplemental Complaint filed Dec. 11, 2020 in U.S. District Court, Delaware, Case #1:19-cv-01126-LPS (43 pages).
Second Amended and Supplemental Complaint filed by Becton, Dickinson and Company et al. on Feb. 25, 2021 in U.S. District Court, Delaware, Case #1:19-cv-01126-LPS (75 pages).
Defendant NeuMoDx's First Supplemental Invalidity Contentions filed Mar. 17, 2021 in U.S. District Court, Delaware, Case #1:19-cv-01126-LPS (55 pages).
Defendant NeuModx's Answer, Affirmative Defenses, and Counterclaims to Plaintiffs' Second and Supplemental Complaint filed Mar. 18, 2021 in U.S. District Court, Delaware, Case #1:19-cv-01126-LPS (67 pages).
Plaintiffs' Answer and/or Reply to Defendants' Counterclaims and Counterclaims-In-Reply filed Apr. 22, 2021 in U.S. District Court, Delaware, Case #1:19-cv-01126-LPS (127 pages).
Claim Construction (Markman) Order dated May 10, 2021 in in U.S. District Court, Delaware, Case #1:19-cv-01126-LPS (30 pages).
Stipulation of Dismissal filed by Plaintiffs Becton, Dickinson and Company, Geneohm Sciences Canada, Inc. and HandyLab, Inc. and Defendants NeuMoDx Molecular, Inc., Qiagen GmbH, and Qiagen North American Holdings, Inc. on Nov. 12, 2021 in U.S. District Court, Delaware, Case # 1:19-cv-01226-LPS (3 pages).

* cited by examiner

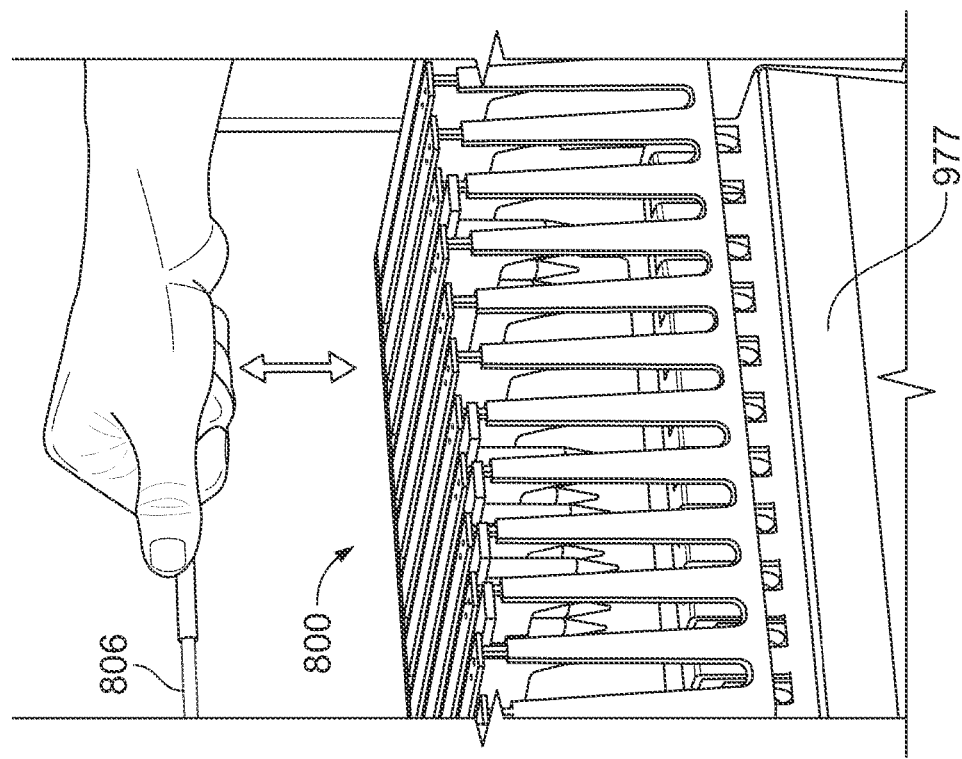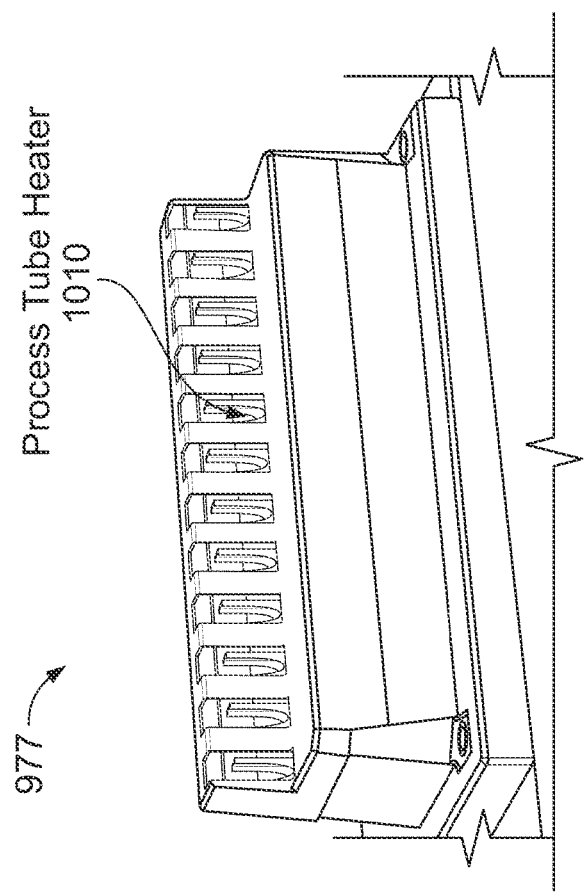
FIG. 2

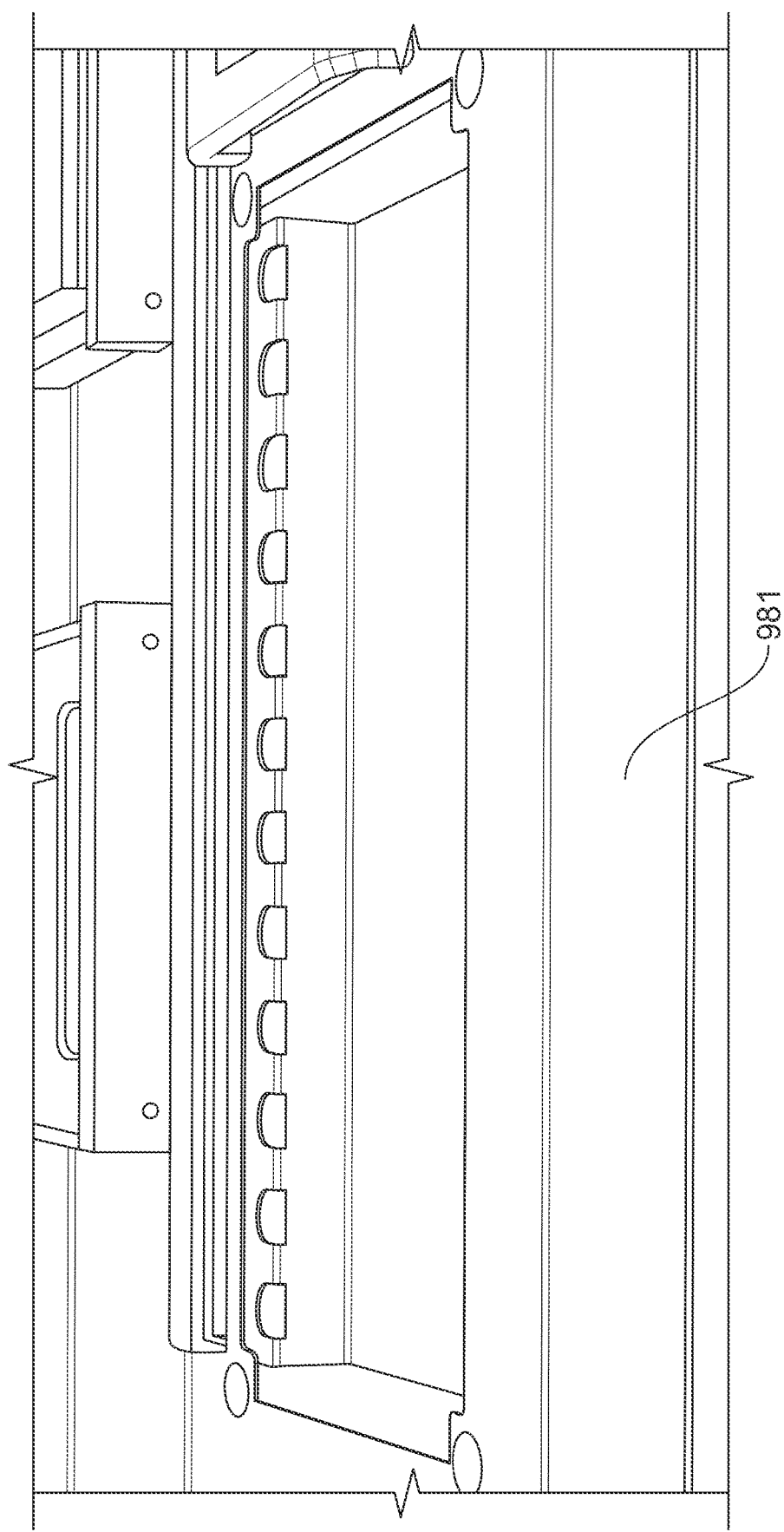

DIAGNOSTIC APPARATUS TO EXTRACT NUCLEIC ACIDS INCLUDING A MAGNETIC ASSEMBLY AND A HEATER ASSEMBLY

CLAIM OF PRIORITY

This application is a continuation of U.S. patent application Ser. No. 16/246,782, filed Jan. 14, 2019 and issued as U.S. Pat. No. 10,844,368 on Nov. 24, 2020, which is a continuation of U.S. patent application Ser. No. 15/017,977, filed Feb. 8, 2016 and issued as U.S. Pat. No. 10,179,910 on Jan. 15, 2019, which is a divisional of U.S. patent application Ser. No. 13/474,980, filed May 18, 2012, now abandoned, which is a continuation of U.S. patent application Ser. No. 12/178,584, filed Jul. 23, 2008 and issued as U.S. Pat. No. 8,182,763 on May 22, 2012, which is a continuation-in-part of U.S. patent application Ser. No. 12/173,023, filed Jul. 14, 2008 and issued as U.S. Pat. No. 8,133,671 on Mar. 13, 2012, which claims priority under 35 U.S.C. § 119(e) to U.S. Provisional Application No. 60/959,437, filed Jul. 13, 2007. U.S. patent application Ser. No. 12/178,584, filed Jul. 23, 2008, is a continuation-in-part of U.S. patent application Ser. No. 12/218,498, filed Jul. 14, 2008 and issued as U.S. Pat. No. 9,186,677 on Nov. 17, 2015, which claims priority under 35 U.S.C. § 119(e) to U.S. Provisional Application No. 60/959,437, filed Jul. 13, 2007. The disclosures of all of the above-referenced prior applications, publications, and patents are considered part of the disclosure of this application, and are incorporated by reference herein in their entirety.

TECHNICAL FIELD

The technology described herein generally relates to racks for holding samples and various reagents, wherein the rack may be used for loading the samples and reagents prior to using the reagents. The technology more particularly relates to racks that accept complementary reagent holders each of which contain a set of reagents for carrying out a predetermined processing operation, such as preparing biological samples for amplifying and detecting polynucleotides extracted from the samples.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Furthermore, the reagents required are of sufficient variety that they typically require different handling from one another and are available from different vendors. Even where reagents can be collected together in a single holder and made ready for use, such as described in copending application Ser. No. 12/218,416, now U.S. Pat. No. 9,701,957, filed by ExpressMail on Jul. 14, 2008 (and entitled "Reagent Tube, Reagent Holder, and Kits Containing Same", in the name of Wilson, et al.) and incorporated herein by reference, it would be beneficial to be able to set up a number of holders for use in batches, and to make them available to liquid dispensing tools that can operate on holders in parallel.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

A rack, comprising: a housing; a plurality of lanes in the housing, and wherein each lane of the plurality of lanes comprises: a first location configured to accept a sample tube; and a second location, configured to accept a reagent holder; and a registration member complementary to a receiving bay of a diagnostic apparatus.

A rack, wherein the registration member comprises two or more positioning pins configured to: ensure that the rack can only be placed in the diagnostic apparatus in a single orientation; and provide stability for the rack when placed in the diagnostic apparatus.

A rack configured to receive a plurality of reagent holders, and to receive a plurality of sample tubes, wherein the reagent holders are in one-to-one correspondence with the sample tubes, and wherein the reagent holders each contain sufficient reagents to extract polynucleotides from the sample and place the polynucleotides into a PCR-ready form, and wherein the rack is configured to be insertable into, and removable from, an apparatus that carries out PCR on the PCR-ready polynucleotides.

A method of carrying out sample preparation on multiple samples in parallel, wherein reagents for carrying out preparation on each sample are contained in respective reagent holders, the holders being supported by a rack, as further described herein. The method, can be carried out automatically by a diagnostic apparatus in which the rack is situated, or can be carried out manually, when the rack is positioned on a horizontal surface, e.g., a laboratory benchtop.

BRIEF DESCRIPTION OF THE DRAWINGS

FIG. 2 shows perspective views of a heater unit and the rack of FIG. 1 positioned in conjunction with the heater unit.

FIGS. 4A-4K show various views of the rack of FIG. 3.

FIG. 5 shows an area of a diagnostic apparatus configured to accept a rack of FIG. 3.

Like reference numerals in the various drawings indicate like elements.

DETAILED DESCRIPTION

Figure 1:
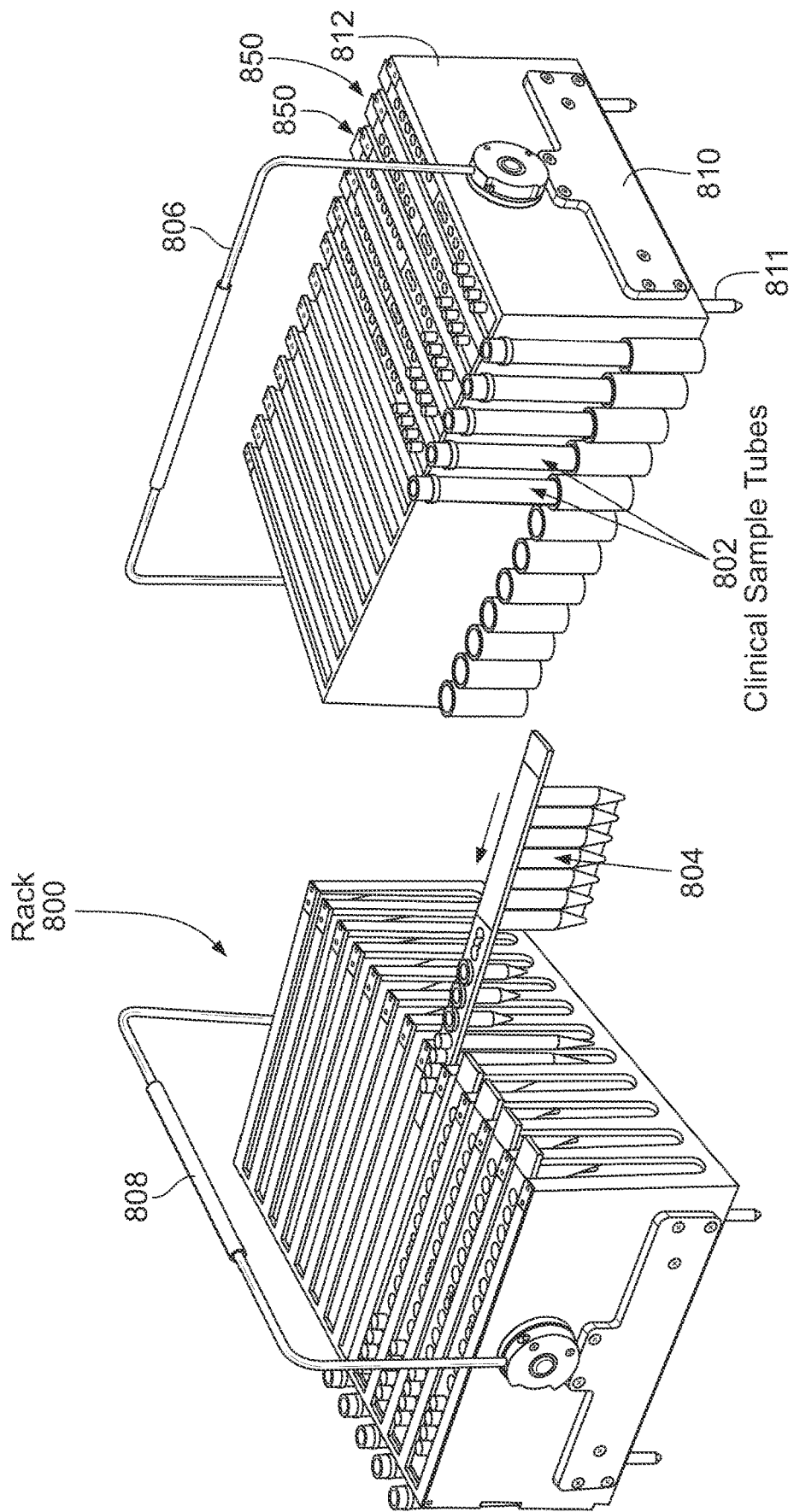
FIG. 1 shows perspective views of an exemplary rack for samples and reagent holders.

Described herein are racks for supporting, carrying, and transporting reagents for various purposes, in particular in connection with sample preparation in a clinical context. The rack permits placement of one or more sample tubes and one or more corresponding holders of reagents, such as analyte specific reagents (ASR's) and/or sample preparation reagents. The samples and holders, when so placed, are positioned to carry out liquid dispensing processes, associated with sample preparation such as for PCR, that minimize cross-sample contamination but permit multiple PCR preparations to be performed from multiple clinical samples, in batches, or in parallel. The racks are configured for use in an automated preparatory apparatus that can carry out sample preparation on samples in more than one holder positioned in a rack simultaneously.

The racks as described herein find particular application to analyzing any nucleic acid containing sample for any purpose, including but not limited to genetic testing, and clinical testing for various infectious diseases in humans.

In various embodiments, preparation of a PCR-ready sample for use in subsequent diagnosis, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid). In some embodiments, the PCR reagent mixture can be in the form of one or more lyophilized pellets, as stored in a container on a reagent holder, and the method can further include reconstituting the PCR pellet with liquid to create a PCR reagent mixture solution. The holders configured for use with racks as described herein provide, in a self-contained manner, all of the reagents required to prepare a PCR-ready sample, or, when delivered to a user in kit form, contain in conjunction with other packages all of the required reagents. Suitable reagents, and protocols for using the same in DNA and RNA extractions can be found in, respectively, copending application Ser. No. 12/172,208, now abandoned, and Ser. No. 12/172,214, now U.S. Pat. No. 8,324,372, both filed Jul. 11, 2008 and incorporated herein by reference.

The racks herein are typically configured for use by an apparatus that carries out automated sample preparation, for example, on multiple samples simultaneously. An exemplary form of such an apparatus is further described herein, and can also be found described in U.S. provisional Patent Application Ser. No. 60/959,437, filed Jul. 13, 2007, incorporated herein by reference in its entirety, and in U.S. patent application Ser. No. 12/173,023, now U.S. Pat. No. 8,133,671, filed on Jul. 14, 2008 (and entitled "Integrated Apparatus for Performing Nucleic Acid Extraction and Diagnostic Testing on Multiple Biological Samples", in the name of Williams, et al.), incorporated by reference herein.

Rack

The racks herein are typically configured to be insertable into, and removable from, a diagnostic or preparatory apparatus, each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and place the polynucleotides into a PCR-ready form. Exemplary reagent holders are further described elsewhere herein and also in copending application Ser. No. 12/218,416, now U.S. Pat. No. 9,701,957, filed by ExpressMail on Jul. 14, 2008 (and entitled "Reagent Tube, Reagent Holder, and Kits Containing Same", in the name of Wilson, et al.) and incorporated herein by reference. An exemplary apparatus is outlined herein, and also described in U.S. patent application Ser. No. 12/173,023, now U.S. Pat. No. 8,133,671, filed on Jul. 14, 2008 (and entitled "Integrated Apparatus for Performing Nucleic Acid Extraction and Diagnostic Testing on Multiple Biological Samples", in the name of Williams, et al.), incorporated by reference herein.

Two perspective views of an exemplary rack 800, configured to accept 12 sample tubes and 12 corresponding reagent holders, in 12 lanes 850, are shown in FIG. 1. A lane 850, as used herein in the context of a rack, is a dedicated region of the rack designed to receive a sample tube and corresponding reagent holder. In the accompanying drawings, not all visible lanes are labeled; usually one lane or a pair of lanes in a given view is given reference number 850. Two perspective views of the same exemplary rack, in conjunction with a heater unit, as further described herein, are shown in FIG. 2.

A rack may accept 2, 4, 6, 8, 10, 12, 16, or 20 samples such as in sample tubes 802, and a corresponding number of holders 804. Thus the embodiment of FIG. 1 configured to receive 12 samples and 12 corresponding reagent holders is exemplary.

A rack is typically configured to accept a number of reagent holders 804, such as those further described herein, the rack being configured to hold one or more such holders, either permitting access on a laboratory benchtop to reagents stored in the holders, or situated in a dedicated region of the apparatus permitting the holders to be accessed by one or more other functions of the apparatus, such as automated pipetting, heating of the process tubes, and magnetic separating of affinity beads. Typically holders 804 each have at least one or more pipette tips, and one or more containers for reagents.

Figure 3:
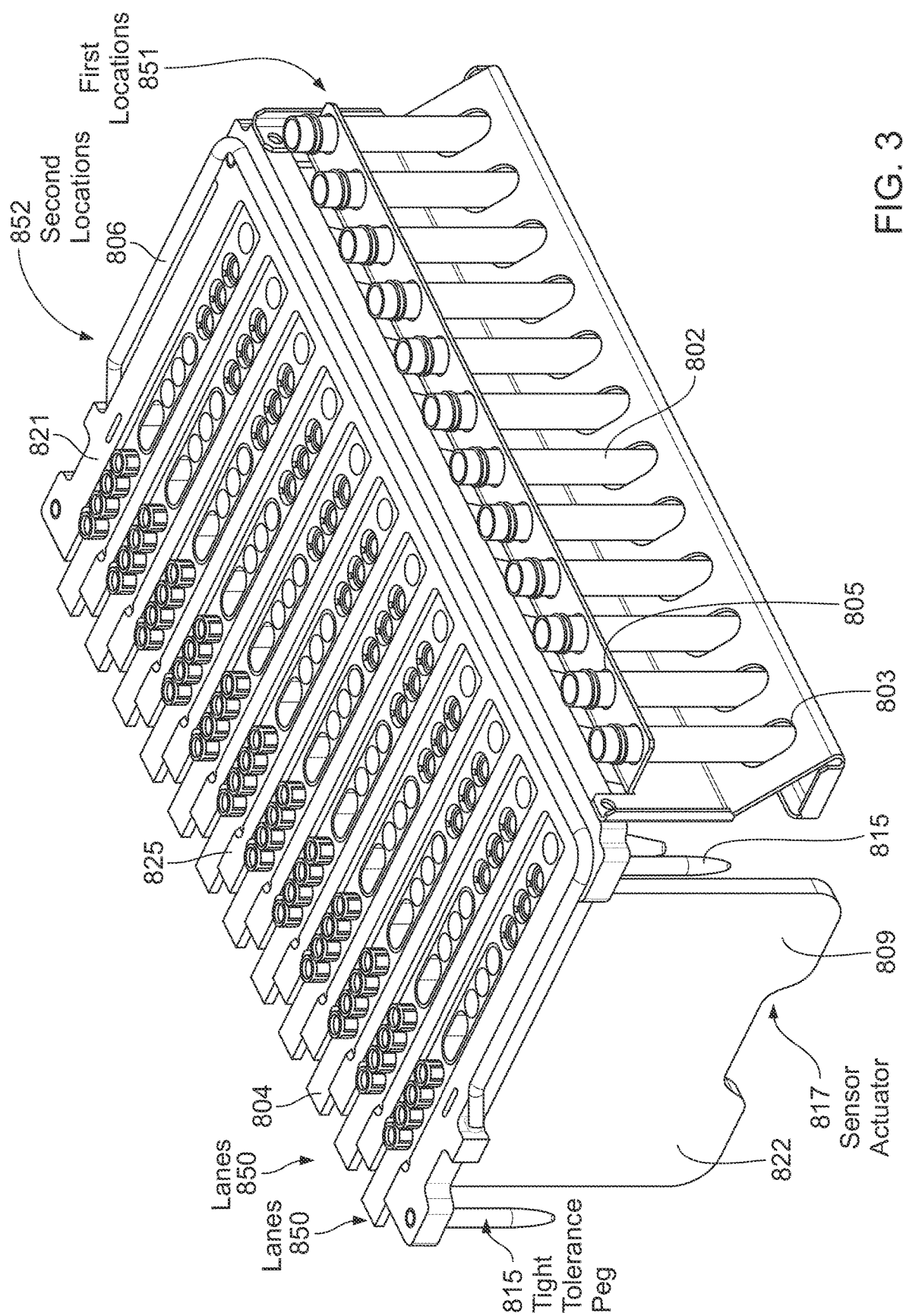
FIG. 3 shows a perspective view of an exemplary rack for samples and reagent holders.
Figure 4A:
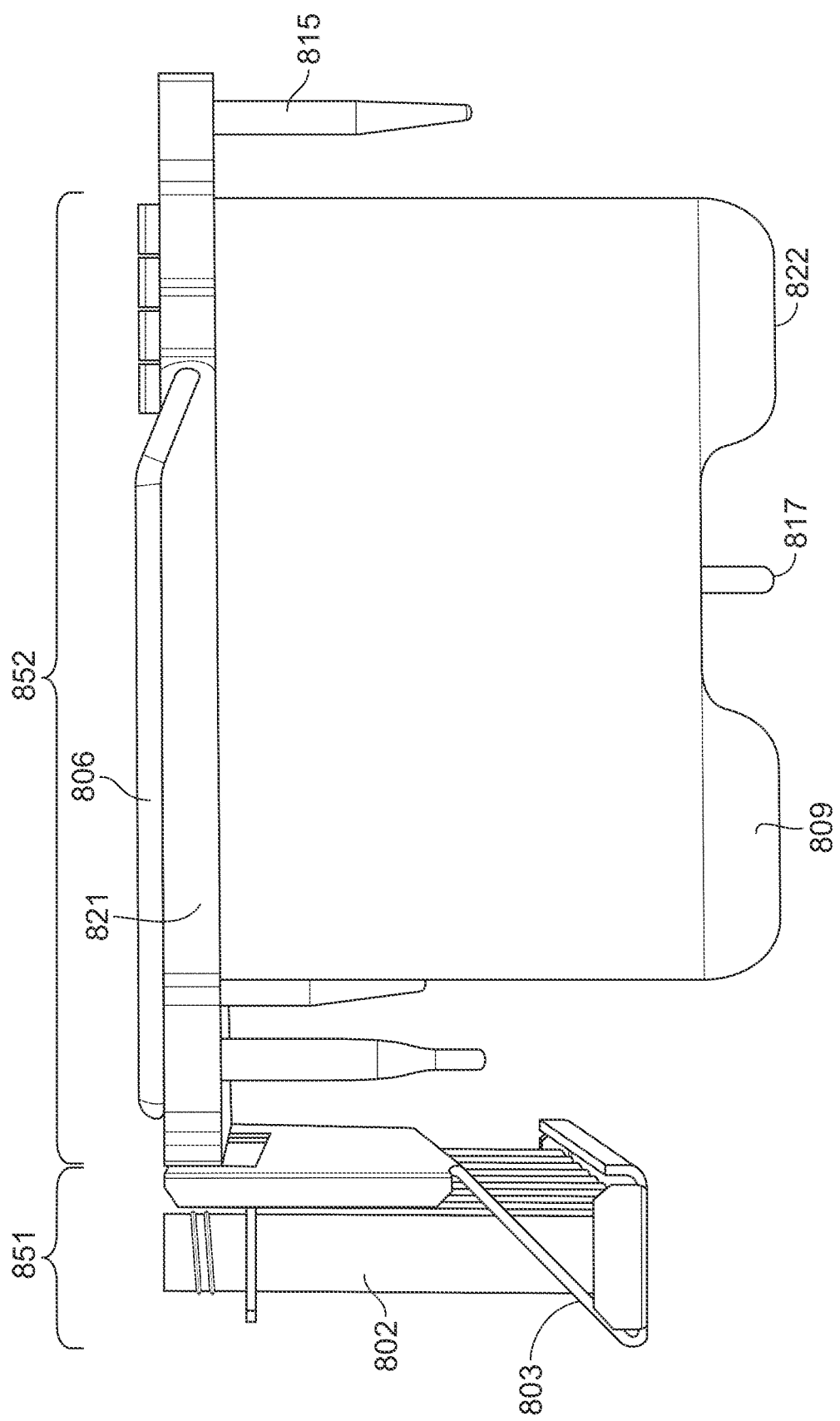
Figure 4B:
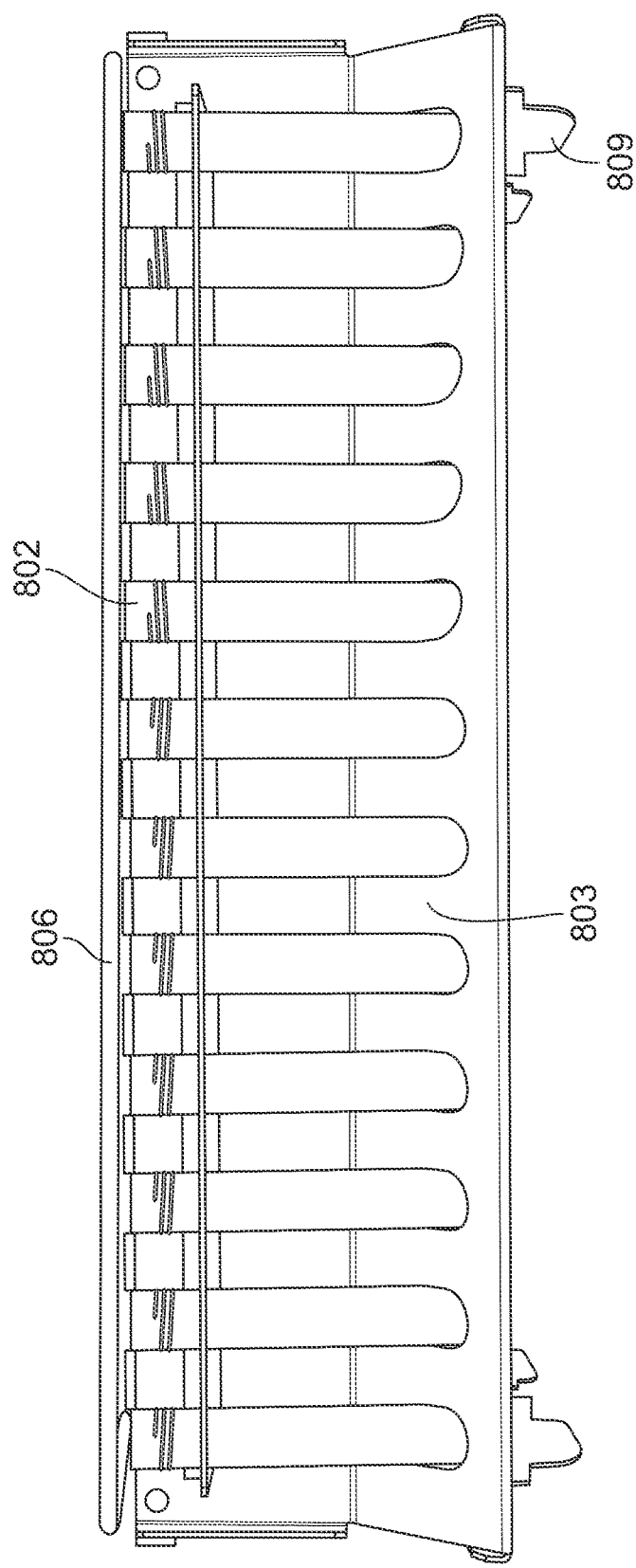
Figure 4C:
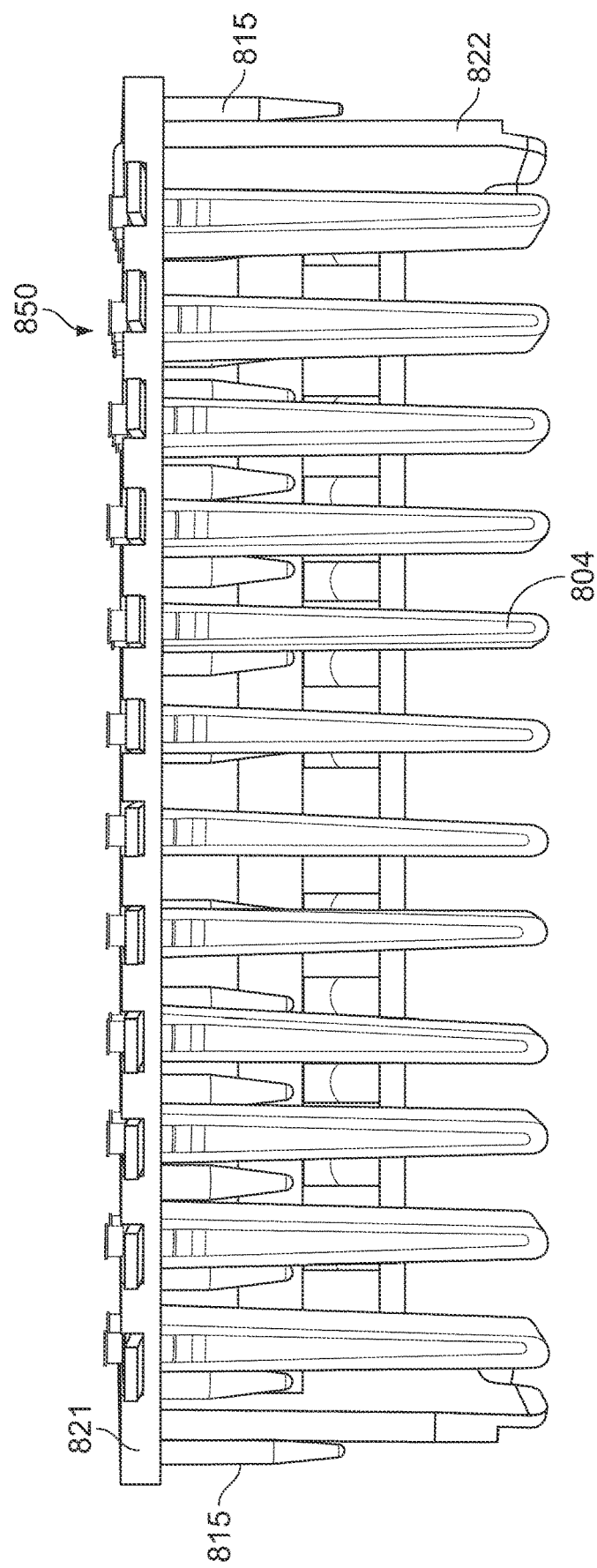
Figure 4D:
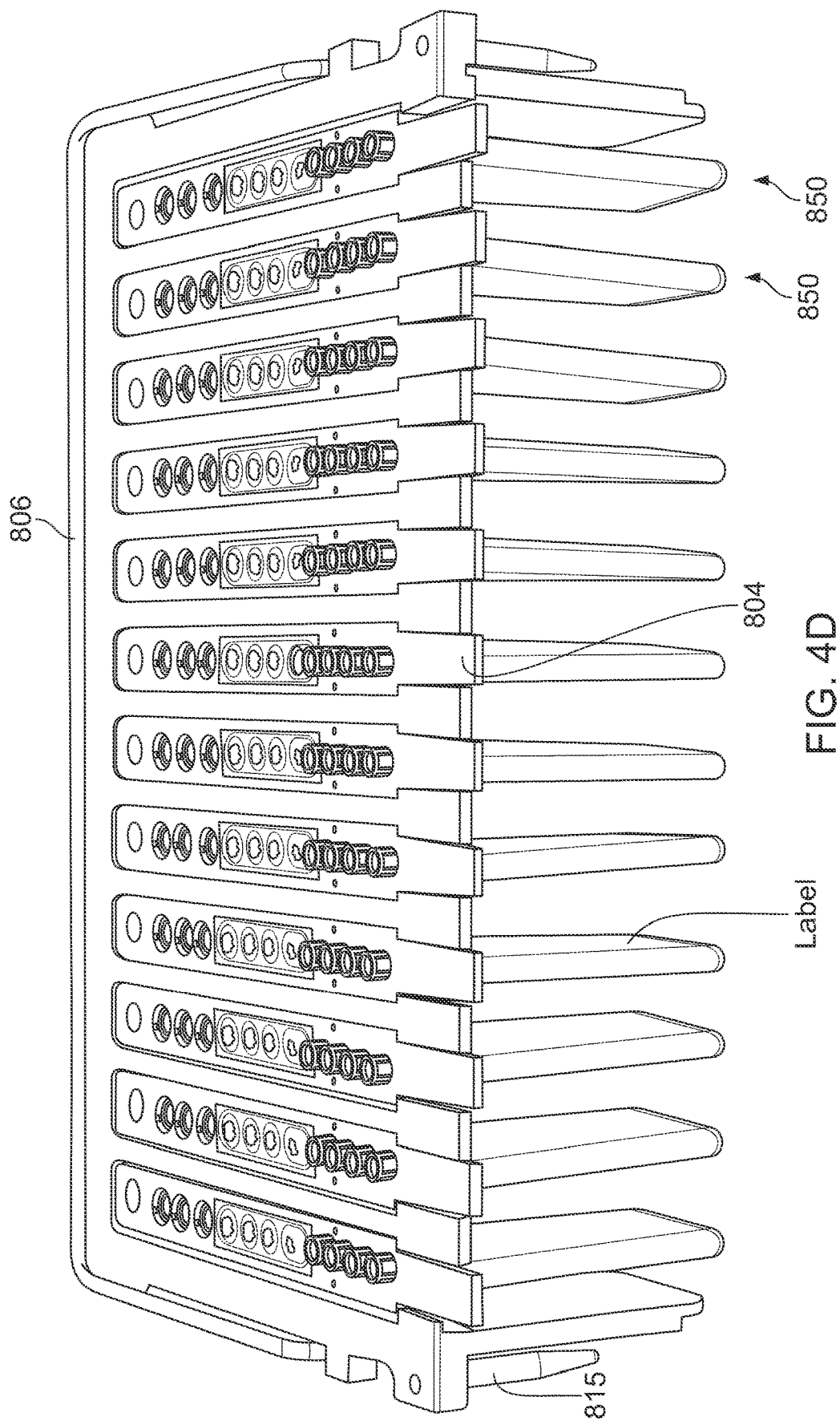
Figure 4E:
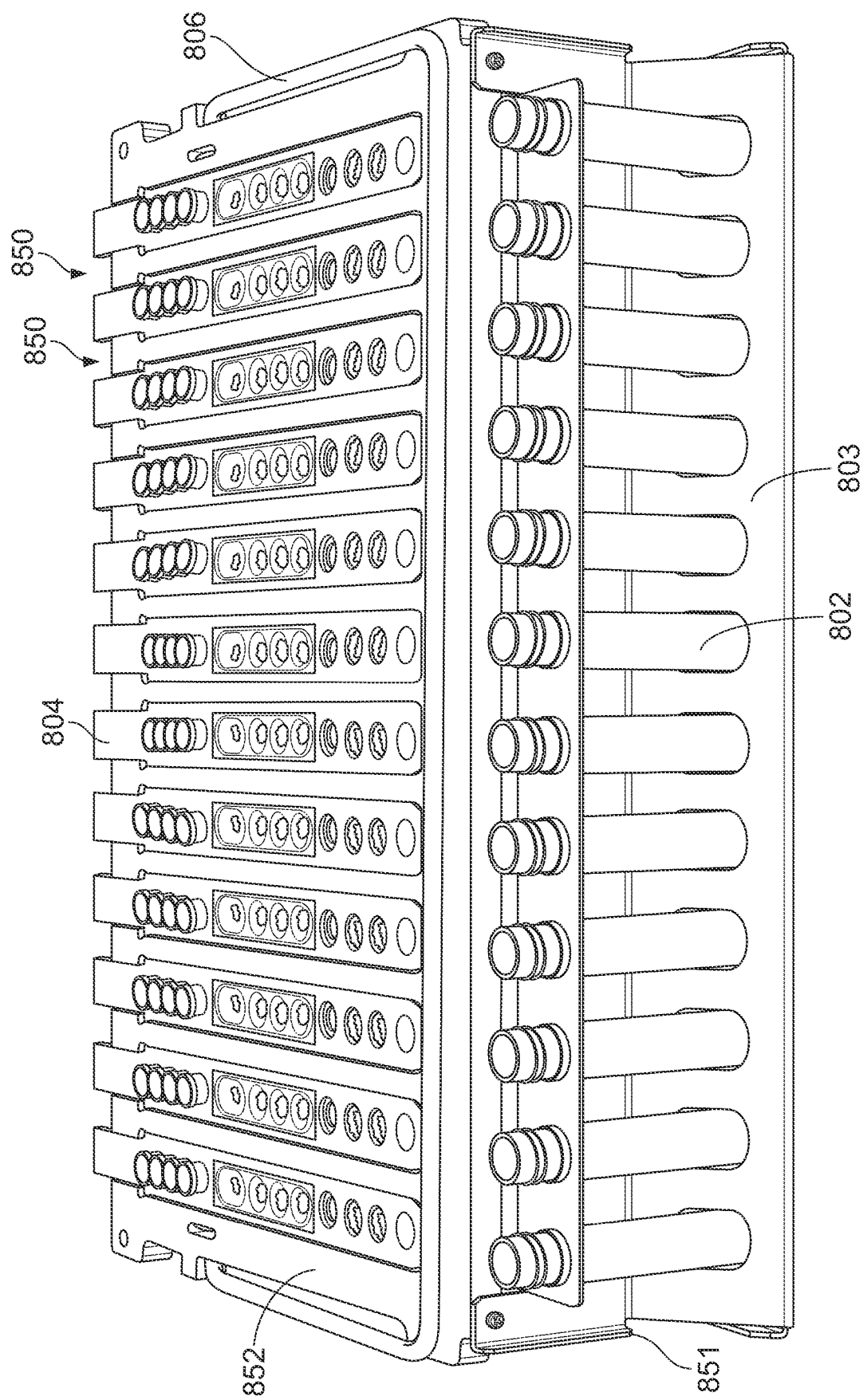
Figure 4F:
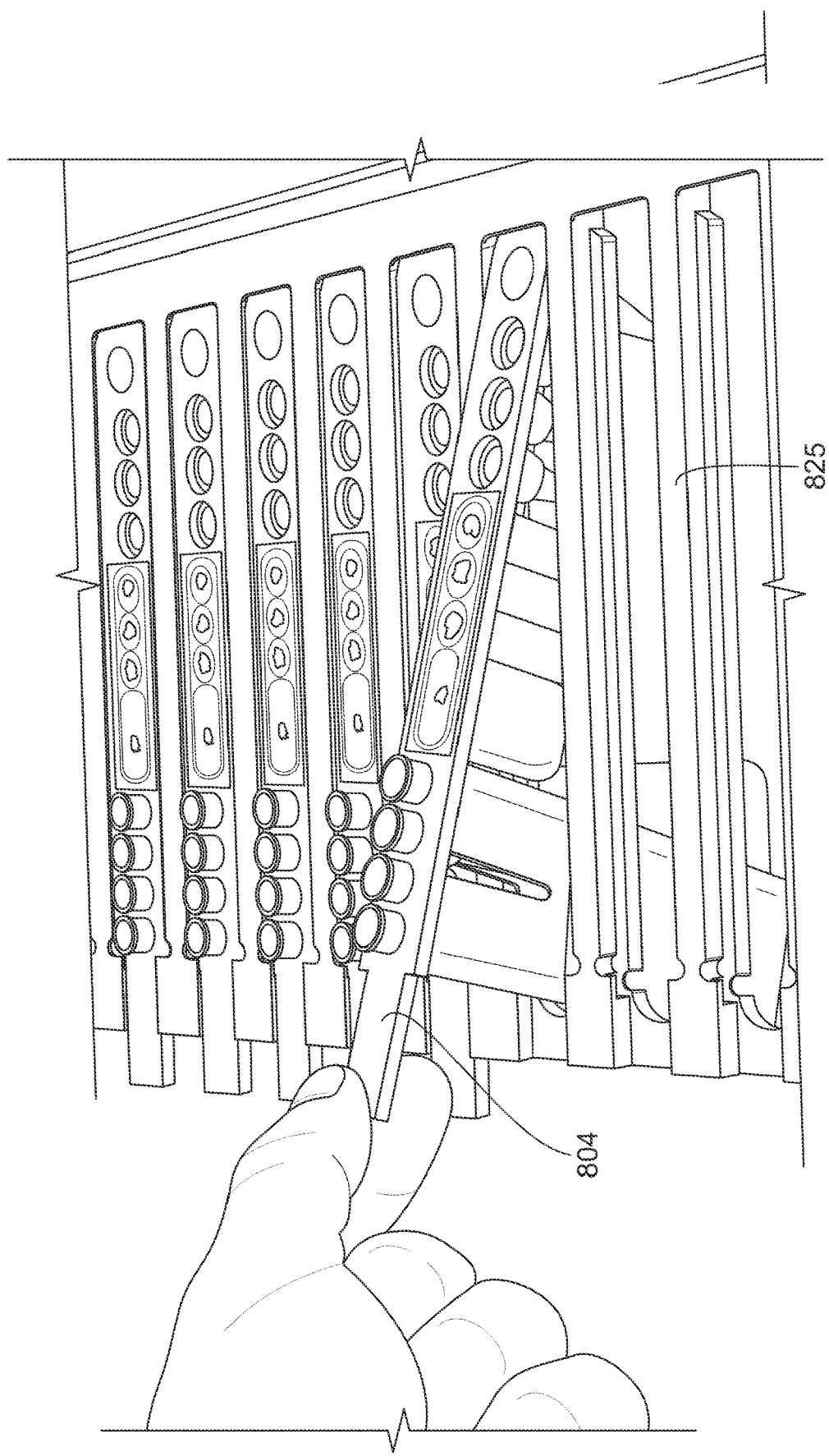
Figure 4G:
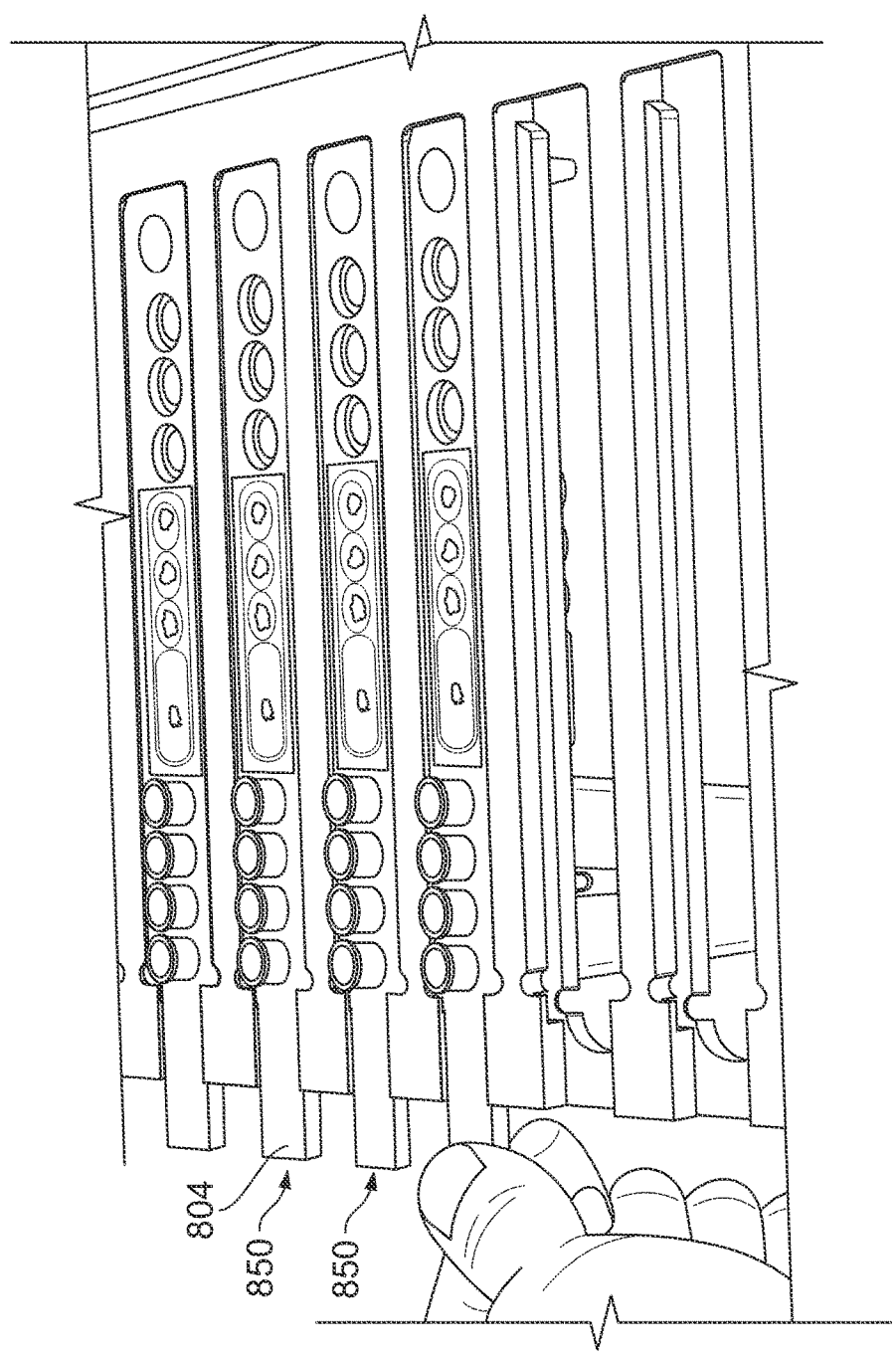
Figure 4H:
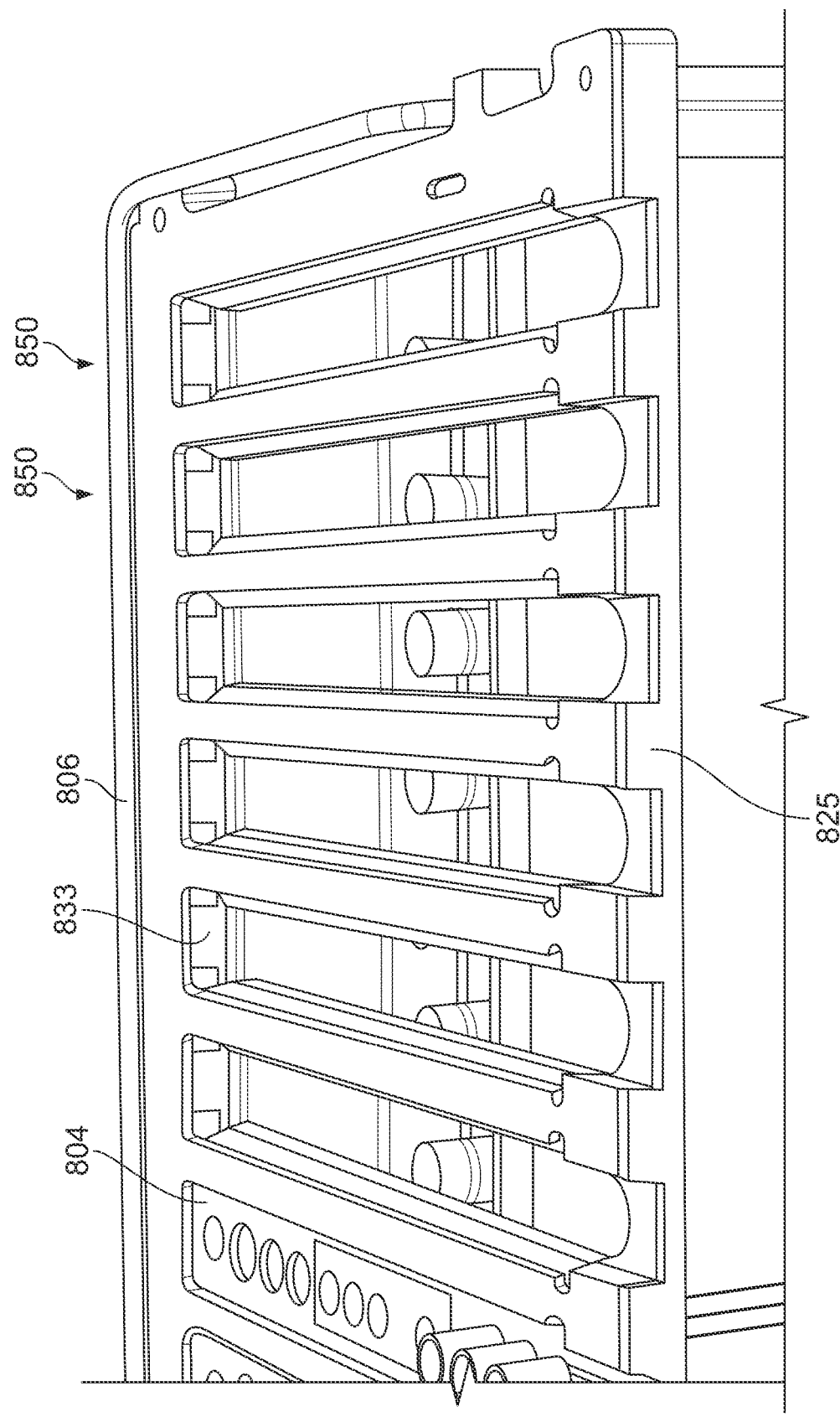
Figure 41:
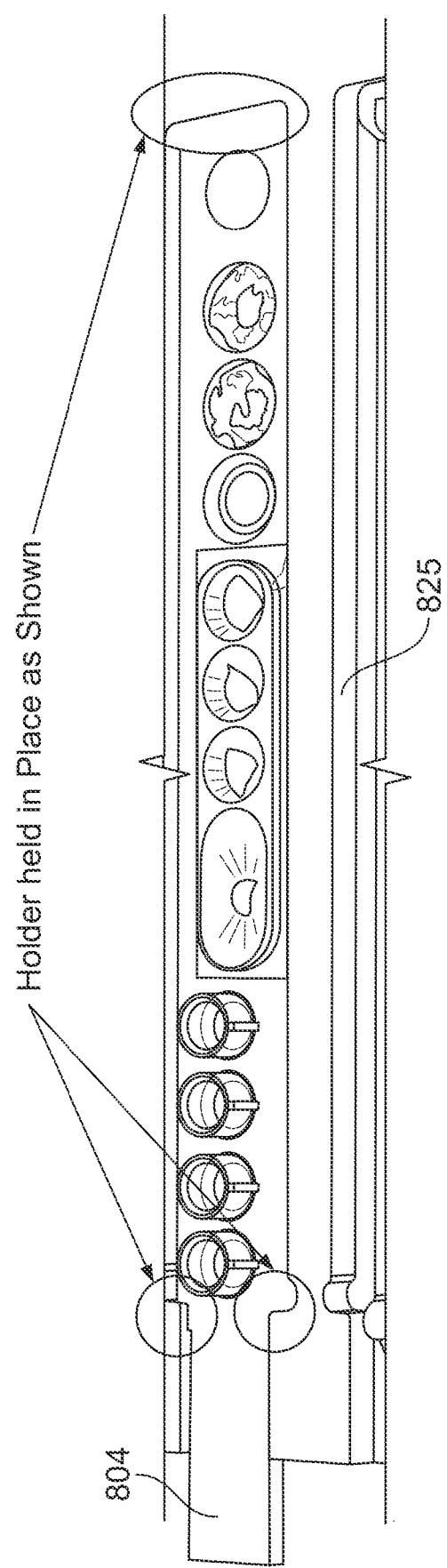
Figure 4J:
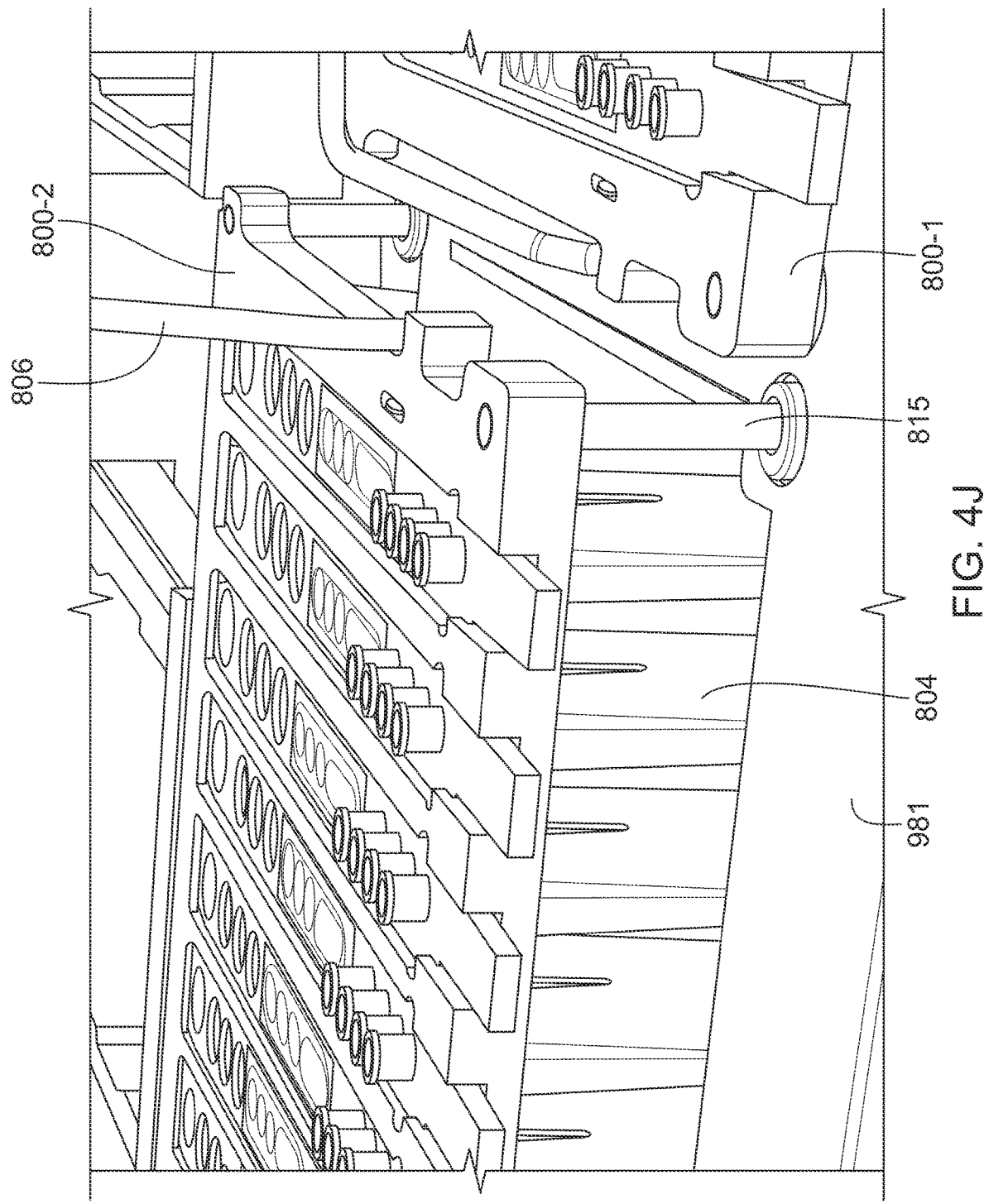
Figure 4K:
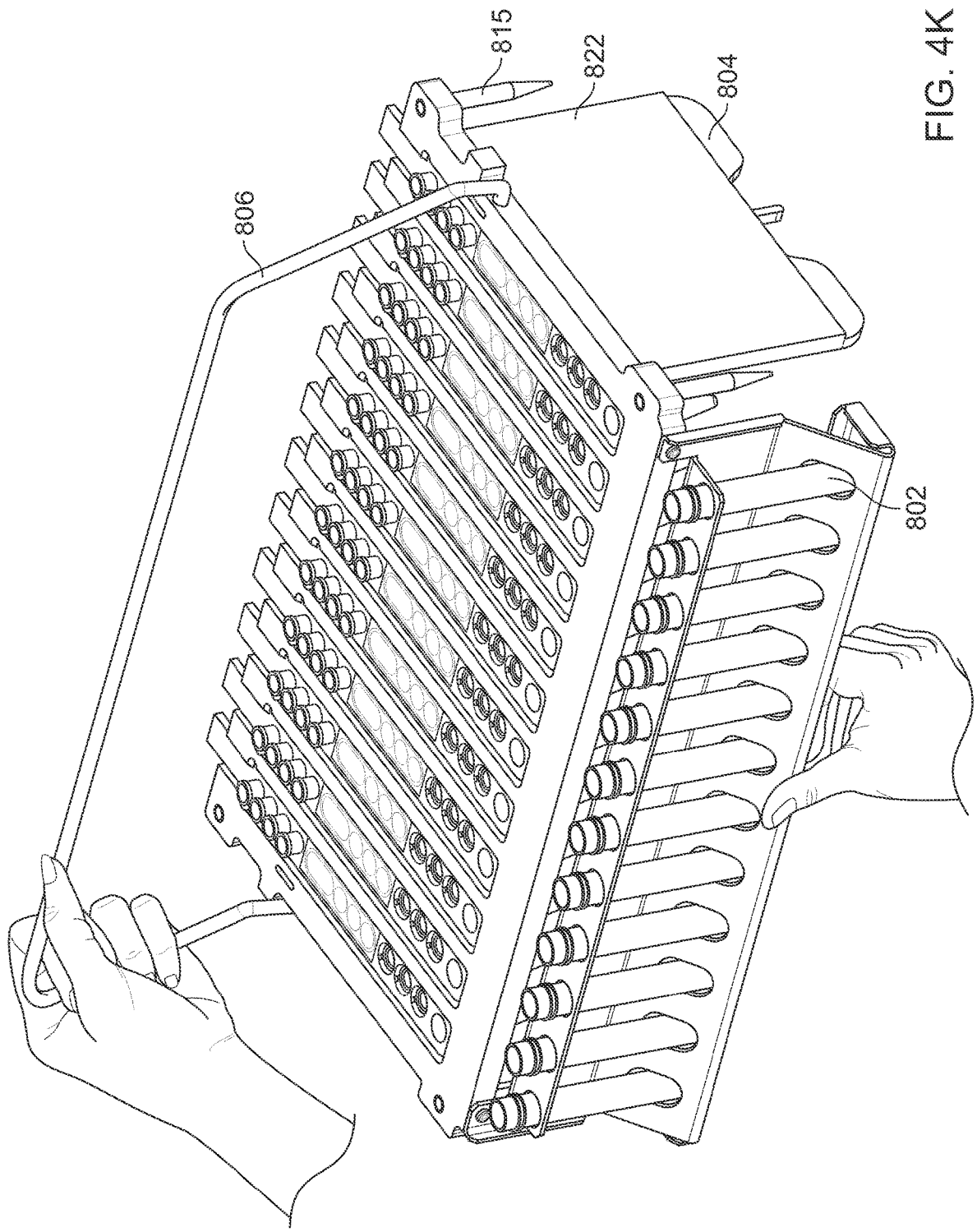

Various views of a second exemplary rack 800, also configured to accept 12 sample tubes and 12 reagent holders, are shown in FIG. 3, and FIGS. 4-4K. Thus, the following views are shown: side plan (FIG. 4A); front plan, showing sample tubes (FIG. 4B); rear plan, showing reagent holders (FIG. 4C); rear elevation, showing reagent holders (FIG. 4D); front elevation, showing sample tubes (FIG. 4E); top, showing insertion of a reagent holder (FIGS. 4F and 4G); top showing slot for inserting a reagent holder (FIG. 4H); top view showing registration of reagent holder (FIG. 4I);

close up of rack in state of partial insertion/removal from apparatus (FIG. 4J); and rack held by handle, removed from apparatus (FIG. 4K).

Figure 6:
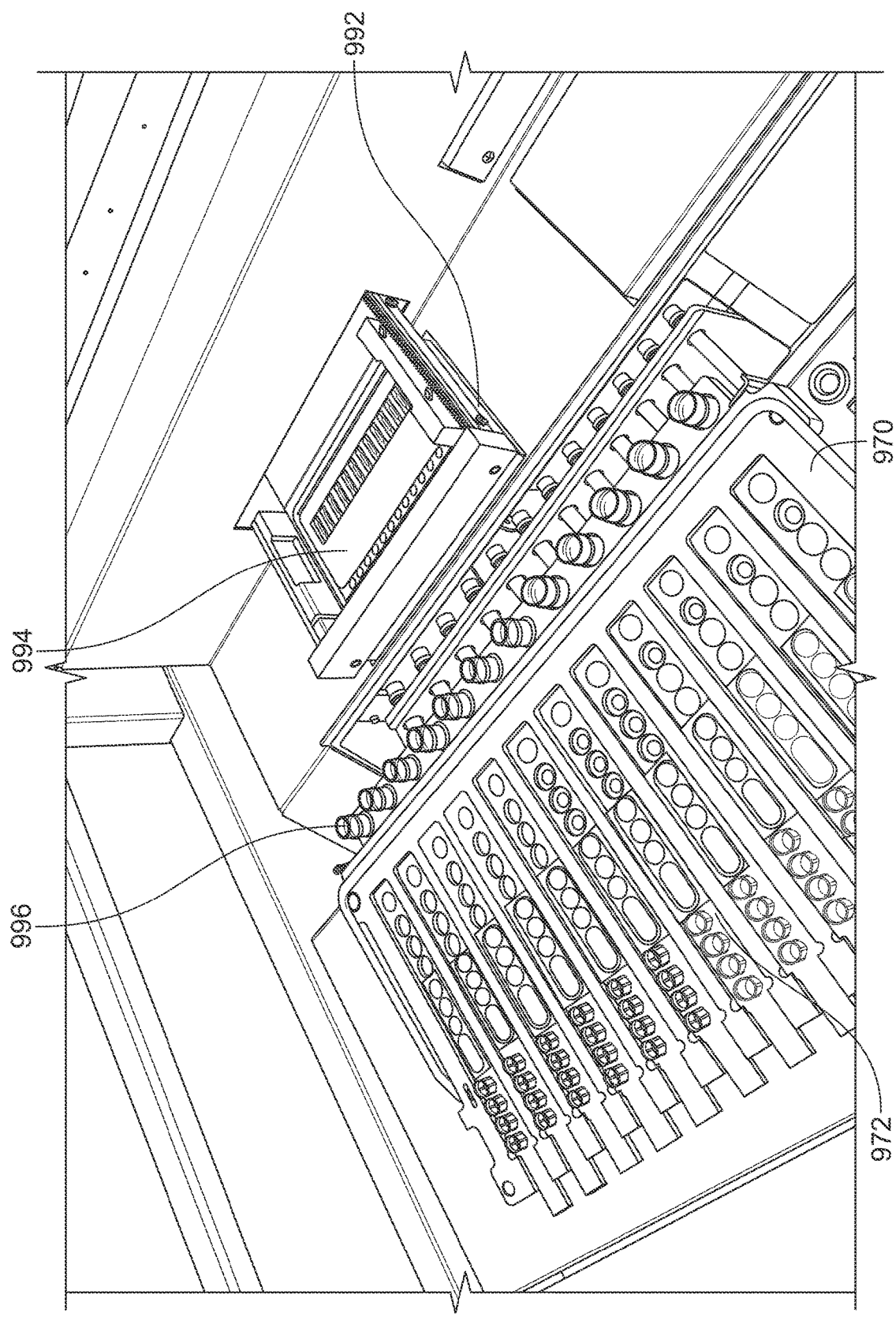
FIG. 6 shows a perspective view of an exemplary rack, carrying a number of sample tubes and reagent holders, and positioned in a diagnostic apparatus.

In FIG. 4J, two racks are visible: rack 800-1 is shown (in part) in position inserted fully into an apparatus 981; rack 800-2 is shown in a state of partial insertion or removal from apparatus 981. A recessed area, such as a receiving bay, in a diagnostic or preparatory apparatus 981, as further described herein, for accepting the exemplary removable rack of FIG. 3 is shown in FIG. 5. A rack, as shown in FIG. 3, situated in the recessed area of FIG. 5 is shown in FIG. 6, in location, in relation to a receiving bay 992 holding a microfluidic cartridge 994 that can be configured to carry out an amplification on a suitably prepared sample, as further described in U.S. patent application Ser. No. 12/173,023, now U.S. Pat. No. 8,133,671, filed on Jul. 14, 2008 (and entitled "Integrated Apparatus for Performing Nucleic Acid Extraction and Diagnostic Testing on Multiple Biological Samples", in the name of Williams, et al.). Other suitably configured recessed areas for receiving other racks differing in shape, appearance, and form, rather than function, are consistent with the description herein.

The two exemplary racks shown in FIGS. 1 and 3 being non-limiting, general features of racks contemplated herein are now described using the two exemplary racks as illustrative thereof. For example, in the embodiments shown here, at least the first lane and the second lane are parallel to one another, a configuration that increases pipetting efficiency. Typically, when parallel to one another, pairs of adjacent sample lanes 850 are separated by 24 mm at their respective midpoints. Other distances are possible, such as 18 mm apart, or 27 mm apart. The distance between the midpoints in dependent on the pitch of the nozzles in the liquid dispensing head, as further described herein. Keeping the spacing in multiples of 9 mm enables easy loading from the rack into a 96 well plate (where typically wells are spaced apart by 9 mm). Typically, also, the rack is such that the plurality of reagent holders in the plurality of lanes are maintained at the same height relative to one another.

The rack is configured to accept a given reagent holder in such a way that the reagent holder snaps or locks reversibly into place, and thereby remains steady while reagents are accessed in it, and while the rack is being carried from one place to another or is being inserted into, or removed from, a diagnostic apparatus.

In each embodiment of FIGS. 1 and 3, each of the second locations in the respective lanes comprises a mechanical key configured to accept the reagent holder in a single orientation. In FIG. 1, it is shown that the reagent holder(s) slide horizontally into vertically oriented slots, one per holder, located in the rack. In such an embodiment, the edge of a connecting member on the holder engages with a complementary groove in the upper portion of a slot. In FIGS. 4F, 4G, and 4I, it is shown that the reagent holder(s) can engage with the rack via a mechanical key that keeps the holders steady and in place. For example, the mechanical key can comprise a raised or recessed portion that, when engaging with a complementary portion of the reagent holder, permits the reagent holder to snap into the second location. It can also be seen in the embodiments shown that the reagent holder has a first end and a second end, and the mechanical key comprises a first feature configured to engage with the first end, and a second feature configured to engage with the second end in such a way that a reagent holder cannot be inserted into the rack the wrong way around. In some embodiments, as shown in FIG. 8H, a sprung metal tab 833 positioned inside the slot serves to keep the holder tightly in place against a stop at the opposite end of the slot.

In certain embodiments the reagent holders each lock into place in the rack, such as with a cam locking mechanism that is recognized as locked audibly and/or physically, or such as with a mechanical key.

The rack can be configured so that the holders, when positioned in it, are aligned for proper pipette tip pick-up using a liquid dispenser as further described herein. Furthermore, the second location of each lane can be deep enough to accommodate one or more pipette tips, such as contained in a pipette tip sheath.

In certain embodiments, the rack is configured to accept the samples in individual sample tubes 802, each mounted adjacent to a corresponding holder 804, for example on one side of rack 800. The sample tubes can be accessible to a sample identification verifier such as a bar code reader, as further described herein. In FIG. 1, a sample tube is held at its bottom by a cylindrical receiving member. In FIG. 3, it is shown that a sample tube can be held at both its top and bottom, such as by a recessed portion 803 configured to receive a bottom of a sample tube, and an aperture 805 configured to hold an upper portion of the sample tube. The aperture can be a ring or an open loop, or a hole in a metal sheet. The recessed portion can be as in FIG. 3, wherein it is an angled sheet of metal housing having a hole large enough to accommodate a sample tube. In alternate embodiments, a sample tube may be held at its lower portion by a member having an aperture and located above a base member on which the bottom of the sample tube rests.

The rack can be designed so that it can be easily removed from the apparatus and carried to and from the laboratory environment external to the apparatus, such as a bench, and the apparatus, for example, to permit easy loading of the sample tube(s) and the reagent holder(s) into the rack. In certain embodiments, the rack is designed to be stable on a horizontal surface, and not easily toppled over during carriage, and, to this end, the rack has one or more (such as 2, 3, 4, 6, 8) feet 809. In certain embodiments, the rack has a handle 806 to ease lifting and moving, and as shown in FIG. 1, the handle can be locked into a vertical position, during carriage, also to reduce risk of the rack being toppled over. The handle can optionally have a soft grip 808 in its middle. In the embodiment of FIG. 3, the carrying handle is positioned about an axis displaced from an axis passing through the center of gravity of the rack when loaded, and is free to fall to a position flush with an upper surface of the rack, under its own weight.

The embodiment of FIG. 1 has a metallic base member 810 having 4 feet 811 that also serve as position locators when inserting the rack into the dedicated portion of the apparatus. The handle is attached to the base member, but other attachments fora handle are possible. The portion of the rack 812 that accepts the samples and holders can be made of plastic, and comprises 12 slots, and may be disposable.

In the embodiment of FIG. 3, the rack comprises a housing, a plurality of lanes in the housing, and wherein each lane of the plurality of lanes comprises: a first location 851 configured to accept a sample tube; and a second location 852, configured to accept a reagent holder; and a registration member complementary to a receiving bay of a diagnostic apparatus. Typically, the housing is made of a metal, such as aluminum, that is both light but also can be machined to high tolerance and is sturdy enough to ensure that the rack remains stable when located in the diagnostic apparatus. The registration member in FIG. 3 comprises four (4) tight tolerance pegs 815, located one per corner of the rack. Such pegs are such that they fit snugly and tightly into complementary holes in a receiving area, such as a recessed area, of the apparatus and thereby stabilize the rack. Other embodiments having, for example, 2, or 3, or greater than 4 such pegs are consistent with the embodiments herein.

In particular, the housing in the embodiment of FIG. 3 comprises a horizontal member 821, and two or more vertical members 822 connected to the horizontal member, and is such that the second location 852 of each respective lane is a recessed portion within the horizontal member. The two or more vertical members 809 in the embodiment of FIG. 3 are configured to permit the rack to free stand thereon. The housing may further comprise two or more feet or runners, attached symmetrically to the first and second vertical members and giving the rack additional stability when positioned on a laboratory bench top.

Furthermore, in the embodiment of FIG. 3, the housing further comprises a plurality of spacer members 825, each of which is disposed between a pair of adjacent lanes. Optionally, such spacer members may be disposed vertically between the lanes.

Although not shown in the FIGs., a rack can further comprise a lane identifier associated with each lane. A lane identifier may be a permanent or temporary marking such as a unique number or letter, or can be an RFID, or bar-code, or may be a colored tag unique to a particular lane.

A rack is configured so that it can be easily placed at the appropriate location in a diagnostic apparatus and gives the user positive feedback, such as audibly or physically, that it is placed correctly. In certain embodiments, the rack can be locked into position. It is desirable that the rack be positioned correctly, and not permitted to move thereafter, so that movement of the liquid dispenser will not be compromised during liquid handling operations. The rack therefore has a registration member to ensure proper positioning. In the embodiment of FIG. 3, the registration member comprises two or more positioning pins configured to ensure that the rack can only be placed in the diagnostic apparatus in a single orientation; and provide stability for the rack when placed in the diagnostic apparatus. The embodiment of FIG. 3 has, optionally, a sensor actuator 817 configured to indicate proper placement of the rack in the diagnostic apparatus. Such a sensor may communicate with a processor 980 to provide the user with a warning, such as an audible warning, or a visual warning communicated via an interface, if the rack is not seated correctly. It may also be configured to prevent a sample preparation process from initiating or continuing if a seating error is detected.

In certain embodiments, the interior of the rack around the location of process tubes in the various holders is configured to have clearance for a heater assembly and/or a magnetic separator as further described herein. For example, the rack is configured so that process chambers on the individual holders are accepted by heater units in a heater assembly as further described herein.

Having a removable rack enables a user to keep a next rack loaded with samples and in line while a previous rack of samples is being processed by the apparatus, so that thereby the apparatus usage time and throughput is maximized.

The rack can also be conveniently cleaned outside of the instrument in case of any sample or reagent spills over it or just as a routine maintenance of laboratory wares.

In certain embodiments the racks have one or more disposable parts.

Reagent Holders

Described herein are reagent holders for holding and transporting reagents for various purposes, in particular sample preparation in a clinical context, and configured to be received by a rack as described herein. The reagent holders also typically provide a container in which various reagents can be mixed one with another and/or with a sample. The reagent holders typically permit snapping in of one or more tubes of analyte specific reagents (ASR's) and/or sample preparation reagents, and carrying out liquid dispensing processes, associated with sample preparation, that minimize cross-sample contamination but permit multiple PCR preparations to be performed from a single clinical sample. The holders are also configured for use in an automated preparatory apparatus that can carry out sample preparation on samples in more than one holder simultaneously.

Figure 7A:
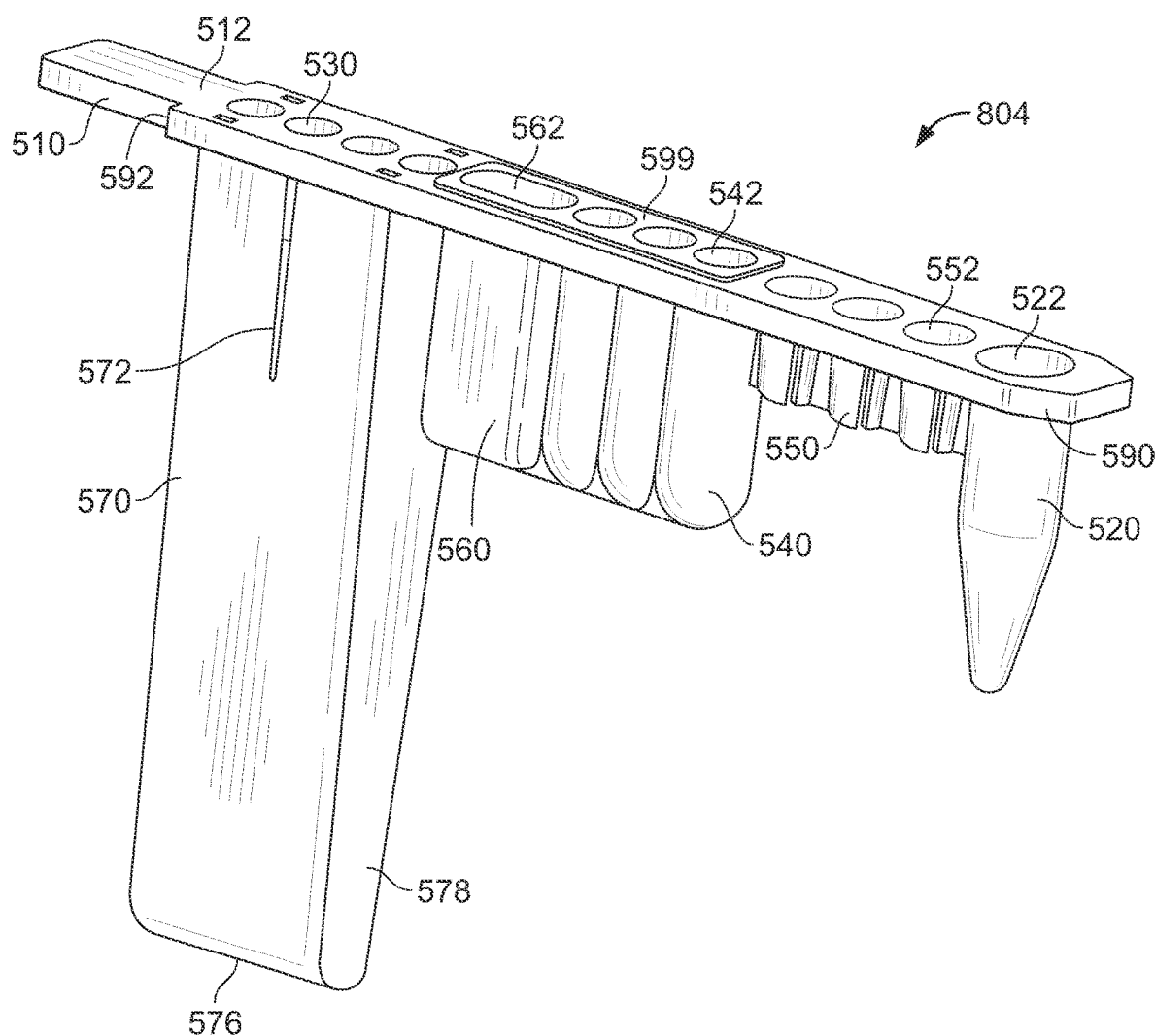
FIGS. 7A and 7B show an exemplary embodiment of a reagent holder having a pipette sheath, in perspective view (FIG. 7A) and underside view (FIG. 7B).
Figure 7B:
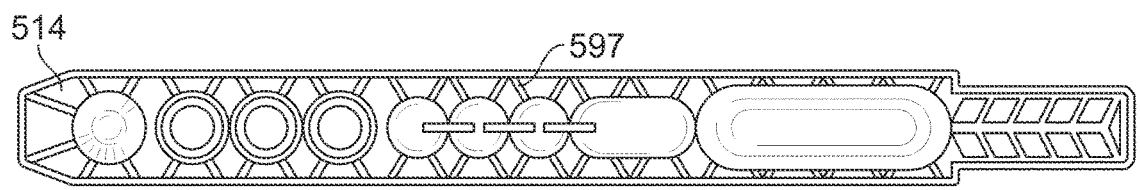

FIGS. 7A and 7B show views of an exemplary holder 804 as further described herein. This exemplary holder, as well as others consistent with the written description herein though not shown as specific embodiments, are now described.

The exemplary holder shown in FIGS. 7A and 7B can also be referred to as a "unitized disposable strip", or a "unitized strip", because it is intended to be used as a single unit that is configured to hold all of the reagents and receptacles necessary to perform a sample preparation, and because it is laid out in a strip format. It is consistent with the description herein, though, that other geometric arrangements of the various receptacles of the holder are contemplated, so that the description is not limited to a linear, or strip, arrangement, but can include a circular or grid arrangement. Accordingly, a rack as described herein can alternatively be configured to accept reagent holders that adopt other shapes than strips. Alternative shapes could be square, rectangular, and circular.

The exemplary holder of FIG. 7A comprises a connecting member 510 having one or more characteristics as follows. Connecting member 510 serves to connect various components of the holder together. Connecting member 510 has an upper side 512 and, opposed to the upper side, an underside 514.

The reagent holder of FIG. 7A is configured to comprise: a process tube 520 affixed to the connecting member and having an aperture 522 located in the connecting member; at least one socket 530, located in the connecting member, the socket configured to accept a disposable pipette tip 580; an optional pipette sheath 570 as further described herein; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown) inserted from the upper side 512 of the connecting member. The lanes of the rack described herein are designed to have sufficient depth and width to accommodate the various reagent tubes, receptacles, process tube, and pipette sheath of a given reagent holder.

In FIG. 7B, a view of underside 514 is shown, having various struts 597 connecting a rim of the connecting member with variously the sockets, process tube, and reagent tubes. Struts 597 are optional, and may be omitted all or in part, or may be substituted by, in all or in part, other supporting pieces that connect various parts of the holder to one another.

The one or more receptacles 550 are configured to accept reagent tubes that contain, respectively, sufficient quantities of one or more reagents typically in solid form, such as in lyophilized form, for carrying out extraction of nucleic acids from a sample that is associated with the holder. The receptacles can be all of the same size and shape, or may be of different sizes and shapes from one another. Receptacles 550 are shown as having open bottoms, but are not limited to such topologies, and may be closed other than the inlet 552 in the upper side of connecting member 510. Preferably the receptacles 550 are configured to accept commonly used containers in the field of laboratory analysis, or containers suitably configured for use with the holder herein. The containers are typically stored separately from the holders to facilitate sample handling, since solid reagents normally require different storage conditions from liquid reagents. In particular many solid reagents may be extremely moisture sensitive.

The snapped-in reagent tubes containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a barcode on a sealing layer on their respective tops.

The containers 554 received by the receptacles 550 may alternatively be an integrated part of the holder and may be the same type of container as the waste chamber and/or the reagent tube(s), or may be different therefrom.

In one embodiment, the containers 554 containing lyophilized reagents, disposed in the receptacles 550, are 0.3 ml tubes that have been further configured to have a star-shaped pattern on their respective bottom interior surfaces. This is so that when a fluid has been added to the lyophilized reagents (which are dry in the initial package), a pipette tip can be bottomed out in the tube and still be able to withdraw almost the entire fluid from the tube. The design of the star-pattern is further described elsewhere in U.S. patent application Ser. No. 12/178,557, now abandoned, filed on even date herewith, and entitled "Reagent Tube", in the name of Handique et al., which application is incorporated herein by reference.

The embodiment of a reagent holder 804 is shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed. Waste chamber 560 is shown as part of an assembly comprising additionally two or more reagent tubes 540. It would be understood that such an arrangement is done for convenience, e.g., of manufacture; other locations of the waste chamber are possible, as are embodiments in which the waste chamber is adjacent a reagent tube, but not connected to it other than via the connecting member.

The embodiment of a reagent holder 804 is shown having a pipette sheath 570. This is an optional component of the holders described herein. It may be permanently or removably affixed to connecting member 510, or may be formed; e.g., moulded, as a part of a single piece assembly for the holder. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. Such cutouts provide ventilation for the pipette tips and also reduce the total amount of material used in manufacture of the holder, and may have various numbers, positions, shapes and sizes, as further described in U.S. patent application Ser. No. 12/218,416, now U.S. Pat. No. 9,701,957, filed by Express-Mail on Jul. 14, 2008, entitled "Reagent Tube, Reagent Holder, and Kits Containing Same", in the name of Wilson, et al., and incorporated herein by reference.

In embodiments having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment having no pipette sheath, could utilize, e.g., a drip tray or a drainage outlet, suitably placed beneath pipette tips located in the one or more sockets, for the same purpose and located under or in the bottom of the rack, as described herein. In addition to catching drips, the pipette tip sheath prevents or inhibits the tips of other reagent holders—such as those that are situated adjacent to the one in question in a rack as further described herein—from touching each other when the tips are picked up and/or dropped off before or after some liquid processing step. Contact between tips in adjacent holders is generally not intended by, for example, an automated dispensing head that controls sample processing on holders in parallel, but the pipette tips being long can easily touch a tip in a nearby holder if the angle when dropping off of the tip deviates slightly from vertical.

Process tube 520 can also be a snap-in tube, rather than being part of an integrated piece. Process tube 520 is typically used for various mixing and reacting processes that occur during sample preparation. For example, cell lysis can occur in process tube 520, as can extraction of nucleic acids, such as DNA or RNA of a patient, and DNA or RNA of a pathogen. Process tube 520 is then advantageously positioned in a location that minimizes, overall, pipette head moving operations involved with transferring liquids to process tube 520. Process tube 520 is also located in the holder in such a position that, when the holder is inserted in a rack as further described herein, the process tube is exposed and accessible to a heater and separator, as further described herein.

Some of the reagents contained in the holder are provided as liquids, and others may be provided as solids. In some embodiments, a different type of container or tube is used to store liquids from those that store the solids.

Reagent tubes 540 are typically configured to hold liquid reagents, one per tube. For example, in reagent holder embodiment 804, three reagent tubes are shown, containing respectively wash buffer, release buffer, and neutralization buffer, each of which is used in a sample preparation protocol.

Reagent tubes 540 that hold liquids or liquid reagents can be sealed with a laminate structure 598 to facilitate long term storage. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum. Various embodiments of a laminate structure are described in U.S. patent application Ser. No. 12/218,416, now U.S. Pat. No. 9,701,957, filed by ExpressMail on Jul. 14, 2008, entitled "Reagent Tube, Reagent Holder, and Kits Containing Same", in the name of Wilson, et al., and incorporated herein by reference. In some embodiments, a raised flat portion 599 facilitates application and removal of laminate 598. Raised surface 599, on the upper side of the connecting member, and surrounding the inlet apertures to the reagent tubes and, optionally, the waste chamber, is an optional feature of the holder.

The containers that hold solid, such as lyophilized reagents, can be sealed across their tops by a metal foil, such as an aluminum foil, with no plastic lining layer, as further described herein.

The reagent holder 804 has a connecting member that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIGS. 7A and 7B. Thus, in FIGS. 7A, and 7B, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

In some embodiments, the holder comprises a registration member such as a mechanical key. Typically such a key is part of the connecting member 510. A mechanical key ensures that the holder is accepted by a complementary member in, for example, a supporting rack as described herein or a receiving bay of an apparatus that controls pipetting operations on reagents in the holder. A mechanical key is normally a particular-shaped cut-out that matches a corresponding cutout or protrusion in a rack or receiving apparatus. Thus, embodiment 804 has a mechanical key 592 that comprises a pair of rectangular-shaped cut-outs on one end of the connecting member. This feature as shown additionally provides for a tab by which a user may gain a suitable purchase when inserting and removing the holder into a rack or another apparatus. Embodiment 804 also has a mechanical key 590 at the other end of connecting member 510. Key 590 is an angled cutout that eases insertion of the holder into a rack, as well as ensures a good registration therein when abutting a complementary angled cut out in a recessed area configured to receive the holder. Other variations of a mechanical key are, of course, consistent with the description herein: for example, curved cutouts, or various combinations of notches or protrusions all would facilitate secure registration of the holder.

In some embodiments, not shown, in FIGS. 7A, 7B, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample is accessible to a sample identification verifier.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport, and thus will not permit reagents to leak out from it.

The holder is typically such that the connecting member, process tube, the two or more reagent tubes, and the waste chamber (if present) are made from a single piece, made from a material such as polypropylene.

The reagent holder for use herein is also typically such that at least the process tube, and the two or more reagent tubes are translucent.

The reagent holders can be disposable, such as intended for a single use, following which it is discarded.

Liquid Dispenser

Additionally, the holders herein are configured, when received by a rack as described elsewhere herein, to accept pipette operations both performed manually by an operator, and by an automated pipette head. An exemplary automated pipette head is described in U.S. provisional application Ser. No. 60/959,437, filed Jul. 13, 2008, and in U.S. patent application Ser. No. 12/173,023, now U.S. Pat. No. 8,133,671, filed Jul. 14, 2008, entitled "Integrated Apparatus for Performing Nucleic Acid Extraction and Diagnostic Testing on Multiple Biological Samples", in the name of Williams, et al., both of which are incorporated herein by reference in their entirety. Typical features of an automated pipette head suitable for operating with holders as described herein include at least: an ability to pick up pipette tips from the one or more sockets, and to return pipette tips to such sockets after use; to strip and discard a pipette tip from a pipette head after use or upon encountering an error; move a pipette tip with precision from one location of a given holder to another so that, for example, liquid reagents can be located and added to solid reagents to make up solutions, and various liquid reagents can be mixed with one another during a sample preparation protocol. Furthermore, it is desirable that such an automated pipette device can operate on several, such as 2, 3, 4, or 6, holders simultaneously when received by a rack, and thereby perform certain operations in parallel. Thus the pipette head should move in three degrees of freedom.

Heater Assembly & Magnetic Separator

The racks as described herein are configured such that reagent holders are positioned so that the process tube is heated by a dedicated heating unit 977, for example situated in an apparatus for carrying out sample preparation on multiple samples in parallel, as shown in FIG. 2. Typically such a heater assembly comprises one or more independently controllable heater units 1010, each of which comprises a heat block configured to heat a process tube in a reagent holder situated in the rack, as further described herein. In one embodiment, a heat element is a power resistor. The right hand panel of FIG. 2 shows how holders loaded in a rack can be positioned in close proximity to a dedicated heating unit. The heating unit is configured to heat the process tube in each of one or more reagent holders positioned in the rack, without unduly heating other portions of the rack, or other containers associated with the reagent holders.

Yet additionally, the holders herein are configured so that the process tube is in close enough proximity to a magnetic assembly that separation of magnetic particles from reagents in solution in the process tube can be accomplished. An exemplary magnetic separator is configured to move one or more magnets relative to the one or more process tubes. Typically, the magnet is mounted in such a way that it can be moved in proximity to the process tubes, either in an automated fashion such as under control of a processor, or manually. The magnet can be made of neodymium (e.g., from K &J Magnetics, Inc.) and can have a magnetic strength of 5,000-15,000 Gauss (Brmax). The poles of the magnets can be arranged such that one pole faces the heat blocks and the other faces away from the heat blocks.

Advantageously, the heater assembly and magnetic separator operate together to permit successive heating and separation operations to be performed on liquid materials in the one or more process tubes without transporting either the liquid materials or the process tubes to different locations to perform either heating or separation. An exemplary heater assembly and magnetic separator are further described in U.S. provisional Patent Application Ser. No. 60/959,437, filed Jul. 13, 2008, and U.S. patent application Ser. No. 12/173,023, now U.S. Pat. No. 8,133,671, filed Jul. 14, 2008, entitled "Integrated Apparatus for Performing Nucleic Acid Extraction and Diagnostic Testing on Multiple Biological Samples", in the name of Williams, et al., and "Ser. No. 12/178,586, now U.S. Pat. No. 9,618,139, entitled "Integrated Heater and Magnetic Separator", in the name of Handique, filed on even date herewith, all of which are incorporated herein by reference in their entirety.

Apparatus Overview

Figure 8:
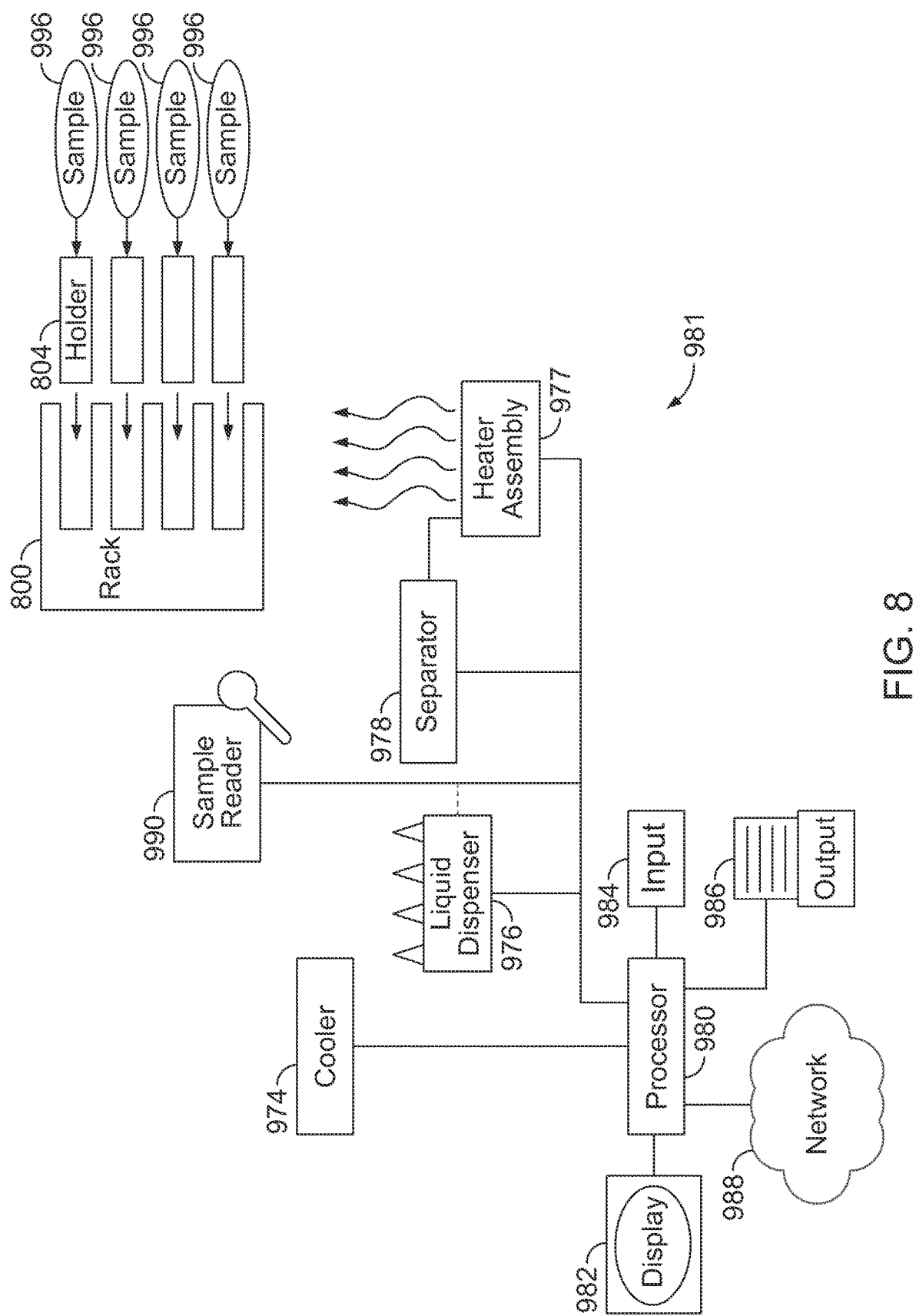
FIG. 8 shows a schematic of an automated apparatus configured to carry out sample preparation using a rack as described herein.

A schematic overview of an apparatus 981 for carrying out automated sample preparation on multiple samples in parallel, according to steps exemplified elsewhere herein, is shown in FIG. 8. The geometric arrangement of the components of system 981 is schematic and not intended to be limiting. The apparatus may additionally comprise (not shown in FIG. 8) a microfluidic cartridge, in a receiving bay, and configured to carry out a diagnostic test on the sample, such as by detecting presence of an amplified polynucleotide in the cartridge. Such additional features are also described in U.S. patent application Ser. No. 12/173,023, now U.S. Pat. No. 8,133,671, filed on Jul. 14, 2008 (and entitled "Integrated Apparatus for Performing Nucleic Acid Extraction and Diagnostic Testing on Multiple Biological Samples", in the name of Williams, et al.).

A processor 980, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 980 can be configured to receive data about a sample to be analyzed, e.g., from a sample reader 990, which may be a barcode reader, an optical character reader, or an RFID scanner (radio frequency tag reader).

Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another. Processor 980 can be optionally further configured to transmit results of an analysis to an output device 986 such as a printer, a visual display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIG. 11, the apparatus 981 is configured to operate in conjunction with a complementary rack 800. Apparatus 981 may be capable of receiving multiple racks, such as 1, 2, 3, 4, or 6 racks.

A rack 800 is itself configured, as further described herein, to receive a number of biological samples 996 in a form suitable for work-up and diagnostic analysis, and a number of holders 804—as further described herein, such as in connection with FIGS. 7A, 7B, that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly can be controlled by the processor 980. Heater assembly 977 operates in conjunction with a separator 978, such as a magnetic separator, that also can be controlled by processor 980 to move into and out of close proximity to one or more processing chambers associated with the holders 804, wherein particles such as magnetic particles are present.

Liquid dispenser 976, which similarly can be controlled by processor 980, is configured to carry out various suck and dispense operations on respective sample, fluids and reagents in the holders 804, to achieve extraction of nucleic acid from the samples. Liquid dispenser 976 can carry out such operations on multiple holders simultaneously. Sample reader 990 is configured to transmit identifying indicia about the sample, and in some instances the holder, to processor 980. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 976 is also configured to take aliquots of fluid containing nucleic acid extracted from one or more samples and direct them to storage area 974, which may be a cooler. Area 974 contains, for example, a PCR tube corresponding to each sample.

Embodiments of the apparatus shown in outline in FIG. 8, as with other exemplary embodiments described herein, are advantageous because they do not require locations within the apparatus suitably configured for storage of reagents. Therefore, the apparatus in FIG. 8 is self-contained and operates in conjunction with holders 804, wherein the holders are pre-packaged with reagents, such as in locations within it dedicated to reagent storage.

The apparatus of FIG. 8 may be configured to carry out operation in a single location, such as a laboratory setting, or may be portable so that they can accompany, e.g., a physician, or other healthcare professional, who may visit patients at different locations. The apparatus is typically provided with a power-cord so that they can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 8 may further be configured, in other embodiments, for multiplexed sample analysis and/or analysis of multiple batches of samples, where, e.g., a single rack holds a single batch of samples. Each component shown in FIG. 8 may therefore be present as many times as there are batches of samples, though the various components may be configured in a common housing.

The apparatus herein can be configured to run on a laboratory benchtop, or similar environment, and can test approximately 45 samples per hour when run continuously throughout a normal working day. Results from individual raw samples are typically available in less than 1 hour.

EXAMPLES

Example 1: Reagent Holder

An exemplary reagent holder consistent with the description herein, and suitable for use with a rack as described herein, has the following dimensions and capacities:
- 180 mm long×22 mm wide×100 mm tall;
- Made from Polypropylene.
- One snapped-in low binding 1.7 ml tube that functions as a process tube.
- 3 built-in tubes that function as receptacles for reagents, as follows:
  - One tube containing 200-1000 µl of wash buffet (0.1 mM Tris, pH 8).
  - One tube containing 200-1000 µl of release solution (40 mM NaOH).
  - One tube containing 200-1000 µl of neutralization solution (330 mM Tris, pH 8.0).
- One built-in tube that functions as a waste chamber (will hold ~4 ml of liquid waste).
- 3 receptacles to accept containers for solid reagents. Snap-in 0.3 ml or 0.65 ml PCR tubes (which are typically stored separately from the reagent holder) are placed in each of these locations, and contain, respectively:
  - lyophilized sample preparation reagents (lysis enzyme mix and magnetic affinity beads).
  - First lyophilized PCR master mix, probes and primers for a first target analyte detection.
  - Second lyophilized PCR master mix, probes and primers for a second target analyte detection (only offered in select cases, such as detection of Chlamydia and Gonorrhea from urine).
- 4 pipette tips located in 4 respective sockets.
- Pipette tip Sheath: The pipette tips have a sheath/drip tray underneath to help capture any drip from the pipette tips after being used, and also to prevent unwanted contamination of the instrument.
- A mechanical key, in conjunction with a spring, allows easy insertion, removal, and positive location of strip in rack.
- One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 2: Exemplary Chemistry Processes Performed by an Automated Instrument

Sample Pre-Processing

For Urine Sample: Take 0.5 ml of urine and mix it with 0.5 ml of collection buffer. Filter the sample through a pre-filter (containing two membranes of 10 micron and 3 micron pore size). Place the sample tube in the position specified for the external sample tube in a 12-holder rack.

For Plasma Sample: Take 0.5 ml of plasma and mix it with 0.5 ml of collection buffer. Place the sample tube in the position specified for the external sample tube in the 12-holder rack.

For GBS swab samples: Take the swab sample and dip it in 1 ml of collection buffer. Place the sample tube in the position specified for the external sample tube in the 12-holder rack.

The sample collection buffer contains 50 mM Tris pH 7, 1% Triton X-100, 20 mM Citrate, 20 mM Borate, 100 mM EDTA, plus 1,000 copies of positive control DNA.

Loading the Instrument and Starting Sample Processing

The following steps may be performed to initiate an analysis on samples in batch.

1. Load PCR tube containing PCR master mix in one of the specified snap-in location of the reagent holder.
2. Load PCR tube containing PCR probes and primers for the target analyte under consideration in the specified location of the reagent holder.
3. In case of two analyte test, load PCR tube containing probes and primers for second analyte in the specified location of the reagent holder.

4. Insert the reagent holder in a 12-holder rack in the same lane as the sample tube under consideration.
5. Prepare and insert reagent holders for other samples in consideration.
6. Load the 12-holder rack in one of the locations in the instrument.
7. Load a 12-sample cartridge in the cartridge tray loading position.
8. Start operation.

Liquid Processing Steps

The following steps may be performed to carry out sample preparation.

1. Using Pipette tip #1, the robot transfers the clinical sample from the external sample tube to the process tube of the reagent holder.
2. Using the same, pipette tip, the robot takes about 100 µl of sample, mixes the lyophilized enzyme and affinity beads, transfers the reagents to the process tube. Mixing is performed in the process tube by 5 suck and dispense operations.
3. The robot places pipette tip #1 at its designated location in the reagent holder.
4. Heat the process tube to 60° C. and maintain it for 10 minutes.
5. After 5 minute of lysis, the robot picks up pipette tip #1 and mixes the contents by 3 suck and dispense operations.
6. The robot places pipette tip #1 at its designated location in the reagent holder.
7. After 10 minutes of lysis, a magnet is moved up the side of the process tube to a middle height of the sample and held at that position for a minute to capture all the magnetic beads against the wall the tube.
8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the process tube.
11. Using the same pipette tip #2, withdraw 100 µl of wash buffer and dispense it in the process tube. During this dispense, the magnet is moved downwards, away from the process tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the process tube.
17. Place pipette tip #2 in its specified location of the reagent holder.
18. Pick up a new pipette tip (tip #3) and withdraw 8-10 µl of release buffer and dispense it over the beads in the process tube.
19. Wait for 1 minute and then perform 45 mixes.
20. Heat the release solution to 85° C. and maintain temperature for 5 minutes.
21. Place pipette tip #3 in its specified location of the reagent holder.
22. Bring magnet up the tube, capture all the beads against the tube wall and move it up and away from the bottom of the tube.
23. Pick up a new pipette tip (tip #4) and withdraw all the release buffer from the process tube and then withdraw 3-10 µl of neutralization buffer, mix it in the pipette tip and dispense it in the PCR tube. (In case of two analyte detections, dispense half of the neutralized DNA solution into first PCR tube and the rest of the solution in the second PCR tube.
24. Using pipette tip #4, mix the neutralized DNA with the lyophilized reagents by 4-5 suck and dispense operations and withdraw the entire solution in the pipette tip.
25. Using pipette tip #4, load 6 µl of the final PCR solution in a lane of the 12-up cartridge.

Real-Time PCR

After all the appropriate PCR lanes of the PCR cartridge are loaded with final PCR solution, the tray containing the cartridge moves it in the PCR Analyzer. The cartridge is pressed by an optical detection read-head against the PCR heater. Heaters activate valves to close either ends of the PCR reactor and real-time thermocycling process starts. After completing appropriate PCR cycles (~45 cycles), the analyzer decides whether the sample has the target. DNA based on the output fluorescence data, and issues an indication of the same.

Example 3: Exemplary Rack

In an exemplary rack for use, in pairs, with a diagnostic instrument, disposable reagent holders (e.g., oriented orthogonally to the front of the instrument) can be contained in one of two, 12-lane racks. The 12 reagent holders in a given rack can register and lock into the rack upon insertion by a user. The rack contains an area for 12 sample lysis tubes and holds the tube bottoms co-planar, thereby allowing the user to orient a bar code on each tube to face the rear of the instrument.

Certain features, permit the racks to be inserted and oriented in the instrument by a minimally trained user. Proper rack placement can be confirmed by feedback to the software. In some embodiments, the racks can be black and color fast (e.g., the color may not appreciably degrade with use or washing with a 10% bleach solution) and the rack material can be dimensionally stable to within 0.1 mm over the operating temperature range of the system. The rack can be designed with provisions to allow the rack to be carried to and from the instrument and to minimize or eliminate the likelihood that the tubes held by the rack will spill when placed on a flat surface.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:
1. A diagnostic apparatus comprising:
a module configured to extract nucleic acid from a first nucleic acid-containing sample and a second nucleic acid-containing sample, wherein the module comprises:
a first lane comprising a first process chamber;
a waste chamber; and
a second lane comprising a second process chamber;
an assembly, wherein the first process chamber and the second process chamber are configured to be received by the assembly, the assembly comprising:

a magnetic assembly configured to apply a magnetic force to the first process chamber and the second process chamber, and a heater assembly configured to apply heat to the first process chamber and the second process chamber, wherein, when the first nucleic acid-containing sample and a first plurality of magnetic affinity beads are received in the first process chamber and when the second nucleic acid-containing sample and a second plurality of magnetic affinity beads are received in the second process chamber, the first nucleic acid-containing sample and the first plurality of magnetic affinity beads are configured to be heated within the first process chamber by the heater assembly and wherein the second nucleic acid-containing sample and the second plurality of magnetic affinity beads are configured to be heated within the second process chamber by the heater assembly, and wherein the magnetic assembly is configured to simultaneously capture or move the first plurality of magnetic affinity beads in the first process chamber and the second plurality of magnetic affinity beads in the second process chamber; and a liquid dispenser configured to perform suck and dispense operations on the first lane and the second lane, wherein when the first nucleic acid-containing sample is received in the first process chamber and when the second nucleic acid-containing sample is received in the second process chamber, the liquid dispenser is configured to withdraw all or substantially all of a liquid of the first nucleic acid-containing sample from the first process chamber, and all or substantially all of a liquid of the second nucleic acid-containing sample from the second process chamber after the use of the heater assembly and the magnetic assembly.

2. The apparatus of claim 1, wherein operations by the heater assembly and the magnetic assembly are performed on liquid material in the first process chamber without transporting either the liquid material or the first process chamber to a different location to perform either heater assembly or magnetic assembly operations.

3. The apparatus of claim 2, wherein the liquid dispenser is configured to perform suck and dispense operations on the first lane and the second lane simultaneously.

4. The apparatus of claim 3, wherein the heater assembly, the magnetic assembly, and the liquid dispenser are configured to be controlled by one or more processors.

5. The apparatus of claim 3, wherein the magnetic assembly is configured to move relative to the first and second process chambers.

6. The apparatus of claim 3, wherein the heater assembly is configured to heat the first and second process chambers without unduly heating another portion of the lanes.

7. The apparatus of claim 2, wherein the liquid dispenser is configured to perform suck and dispense operations on the first lane and the second lane in parallel.

8. A diagnostic apparatus comprising:
a module configured to extract nucleic acid from a first nucleic acid-containing sample and a second nucleic acid-containing sample, wherein the module comprises:
a first lane comprising a first process chamber;
a waste chamber; and
a second lane comprising a second process chamber;
an assembly, wherein the first process chamber and the second process chamber are configured to be received by the assembly, the assembly comprising:
a magnetic assembly configured to apply a magnetic force to the first process chamber and the second process chamber, and a heater assembly configured to apply heat to the first process chamber and the second process chamber, wherein the heater assembly is configured to heat the first and second process chambers without unduly heating another portion of the lanes, wherein, when the first nucleic acid-containing sample and a first plurality of magnetic affinity beads are received in the first process chamber and when the second nucleic acid-containing sample and a second plurality of magnetic affinity beads are received in the second process chamber, the first nucleic acid-containing sample and the first plurality of magnetic affinity beads are configured to be heated within the first process chamber by the heater assembly and wherein the second nucleic acid-containing sample and the second plurality of magnetic affinity beads are configured to be heated within the second process chamber by the heater assembly, and wherein the magnetic assembly is configured to simultaneously capture or move the first plurality of magnetic affinity beads in the first process chamber and the second plurality of magnetic affinity beads in the second process chamber; and a liquid dispenser configured to perform suck and dispense operations on the first lane and the second lane.

9. The apparatus of claim 8, wherein operations by the heater assembly and the magnetic assembly are performed on liquid material in the first process chamber without transporting either the liquid material or the first process chamber to a different location to perform either heater assembly or magnetic assembly operations.

10. The apparatus of claim 9, wherein the magnetic assembly is configured to move relative to the first and second process chambers.

11. The apparatus of claim 10, wherein the heater assembly is configured to be controlled by a processor.

12. The apparatus of claim 9, wherein the liquid dispenser is configured to be controlled by a processor.

13. The apparatus of claim 12, wherein the liquid dispenser is configured to perform suck and dispense operations on the first lane and the second lane simultaneously.

14. The apparatus of claim 12, wherein the liquid dispenser is configured to perform suck and dispense operations on the first lane and the second lane in parallel.

15. A diagnostic apparatus comprising:
a module configured to extract nucleic acid from a first nucleic acid-containing sample and a second nucleic acid-containing sample, wherein the module comprises:
a first lane comprising a first process chamber;
a waste chamber; and
a second lane comprising a second process chamber;
an assembly, wherein the first process chamber and the second process chamber are configured to be received by the assembly, the assembly comprising:
a magnetic assembly configured to apply a magnetic force to the first process chamber and the second process chamber, and a heater assembly configured to apply heat to the first process chamber and the second process chamber, wherein operations by the heater assembly and the magnetic assembly are performed on liquid material in the first process chamber without transporting either the liquid material or the first process chamber to a different location to perform either heater assembly or magnetic assembly operations, wherein, when the first nucleic acid-containing sample and a first plurality of magnetic affinity beads are received in the first process chamber and when the second nucleic acid-containing sample and a second plurality of magnetic affinity beads are received in the second process chamber, the first nucleic acid-containing sample and the first plurality of magnetic affinity beads are configured to be heated within the first process chamber by the heater assembly and wherein the second nucleic acid-containing sample and the second plurality of magnetic affinity beads are configured to be heated within the second process chamber by the heater assembly, and wherein the magnetic assembly is configured to simultaneously capture or move the first plurality of magnetic affinity beads in the first process chamber and the second plurality of magnetic affinity beads in the second process chamber; and a liquid dispenser configured to perform suck and dispense operations on the first lane and the second lane.

16. The apparatus of claim 15, wherein the liquid dispenser is configured to perform suck and dispense operations on the first lane and the second lane simultaneously.

17. The apparatus of claim 15, wherein the magnetic assembly is configured to move relative to the first and second process chambers.

18. The apparatus of claim 15, wherein the liquid dispenser is configured to perform suck and dispense operations on the first lane and the second lane in parallel.

19. The apparatus of claim 15, wherein the liquid dispenser is configured to withdraw an entire solution from each process chamber.

20. The apparatus of claim 15, wherein the heater assembly, the magnetic assembly, and the liquid dispenser are configured to be controlled by one or more processors.

* * * * *